(12) United States Patent (10) Patent No.: US 9,491,415 B2
Deitz et al. (45) Date of Patent: Nov. 8, 2016

(54) METHODS, SYSTEMS AND DEVICES FOR SPINAL SURGERY POSITION OPTIMIZATION

(71) Applicant: ORTHO KINEMATICS, INC., Austin, TX (US)

(72) Inventors: Adam Deitz, Austin, TX (US); Richard K. Grant, Sudbury, MA (US)

(73) Assignee: ORTHO KINEMATICS, INC., Austin, TX (US)

( * ) Notice: Subject to any disclaimer, the term of this patent is extended or adjusted under 35 U.S.C. 154(b) by 0 days.

(21) Appl. No.: 14/874,813

(22) Filed: Oct. 5, 2015

(65) Prior Publication Data

US 2016/0028998 A1 Jan. 28, 2016

Related U.S. Application Data

(63) Continuation of application No. 13/882,022, filed as application No. PCT/US2011/064404 on Dec. 12, 2011.

(60) Provisional application No. 61/422,283, filed on Dec.
(Continued)

(51) Int. Cl.
*H04N 7/18* (2006.01)
*A61B 5/11* (2006.01)
(Continued)

(52) U.S. Cl.
CPC ............. *H04N 7/183* (2013.01); *A61B 5/1079* (2013.01); *A61B 5/1121* (2013.01);
(Continued)

(58) Field of Classification Search
None
See application file for complete search history.

(56) References Cited

U.S. PATENT DOCUMENTS 3,678,190 A 7/1972 Cook
4,210,317 A 7/1980 Spann et al.
(Continued)

FOREIGN PATENT DOCUMENTS

AU 2007238017 B2 3/2013
DE 20009875 U1 9/2000
(Continued)

OTHER PUBLICATIONS

Biomedical Business & Technology, "Minimally invasive procedures are the name of the game", Jun. 5, 2008. http://search.proquest.com/professional/docview/1083067354?accountid=157282.
(Continued)

*Primary Examiner* — Anner Holder
*Assistant Examiner* — William Adrovel
(74) *Attorney, Agent, or Firm* — Shartsis Friese LLP; Cecily Anne O'Regan

(57) ABSTRACT

Three components are proposed, each having at its core a system for producing measurements of the relative motion of anatomical structures of mammals (the "measurement system"). The measurement system in this case would be comprised of an apparatus for imaging the joint of through a prescribed motion, and a process and mechanism for deriving quantitative measurement output data from the resulting images. The components of the present invention include: (1) a software device for reporting measurement output of the measurement system and for allowing users to interact with the measurement output data; (2) an apparatus and method for utilizing measurement output of the measurement system for therapeutic and surgical applications such as surgical navigation and patient positioning during a therapeutic procedure; and (3) an apparatus providing input image data for the measurement system that assists with the imaging of joints connecting anatomical regions that are in motion during operation.

37 Claims, 30 Drawing Sheets

Related U.S. Application Data 13, 2010, provisional application No. 61/444,265, filed on Feb. 18, 2011, provisional application No. 61/451,548, filed on Mar. 10, 2011, provisional application No. 61/453,236, filed on Mar. 16, 2011, provisional application No. 61/454,601, filed on Mar. 21, 2011, provisional application No. 61/499,272, filed on Jun. 21, 2011.

(51) Int. Cl.
  *G06F 19/00* (2011.01)
  *A61B 5/107* (2006.01)
  *A61B 5/06* (2006.01)
  *A61F 2/44* (2006.01)
  *G06T 7/00* (2006.01)
  *A61B 6/00* (2006.01)
  *A61B 6/03* (2006.01)
  *A61B 5/00* (2006.01)

(52) U.S. Cl.
  CPC .......... *A61B 5/4566* (2013.01); *A61B 5/7275* (2013.01); *A61B 5/7278* (2013.01); *A61B 5/746* (2013.01); *A61B 34/10* (2016.02); *G06F 19/321* (2013.01); *H04N 7/18* (2013.01); *A61B 5/06* (2013.01); *A61B 5/107* (2013.01); *A61B 5/1071* (2013.01); *A61B 5/1075* (2013.01); *A61B 5/1128* (2013.01); *A61B 5/4528* (2013.01); *A61B 5/743* (2013.01); *A61B 5/744* (2013.01); *A61B 5/7435* (2013.01); *A61B 6/032* (2013.01); *A61B 6/487* (2013.01); *A61B 6/505* (2013.01); *A61B 34/20* (2016.02); *A61B 90/36* (2016.02); *A61B 2034/105* (2016.02); *A61B 2034/107* (2016.02); *A61F 2/44* (2013.01); *G06T 7/0014* (2013.01); *G06T 7/0065* (2013.01); *G06T 2207/30012* (2013.01)

(56) References Cited

U.S. PATENT DOCUMENTS

| | | |
|---|---|---|
| 4,404,590 A | 9/1983 | Mayer et al. |
| 4,611,581 A | 9/1986 | Steffee |
| 4,803,734 A | 2/1989 | Onishi et al. |
| 4,805,602 A | 2/1989 | Puno et al. |
| 4,922,909 A | 5/1990 | Little et al. |
| 5,000,165 A | 3/1991 | Watanabe |
| 5,019,081 A | 5/1991 | Watanabe |
| 5,058,602 A | 10/1991 | Brody |
| 5,090,042 A | 2/1992 | Bejjani et al. |
| 5,099,859 A | 3/1992 | Bell |
| 5,129,900 A | 7/1992 | Asher et al. |
| 5,203,346 A | 4/1993 | Fuhr et al. |
| 5,316,018 A | 5/1994 | O'Brien |
| 5,320,640 A | 6/1994 | Riddle et al. |
| 5,330,417 A | 7/1994 | Petersen et al. |
| 5,349,956 A | 9/1994 | Bonutti |
| 5,400,800 A | 3/1995 | Jain et al. |
| 5,414,811 A | 5/1995 | Parulski et al. |
| 5,427,116 A | 6/1995 | Noone |
| 5,442,729 A | 8/1995 | Kramer et al. |
| 5,443,505 A | 8/1995 | Wong et al. |
| 5,445,152 A | 8/1995 | Bell et al. |
| 5,474,555 A | 12/1995 | Puno et al. |
| 5,505,208 A | 4/1996 | Toomim et al. |
| 5,548,326 A | 8/1996 | Michael |
| 5,575,792 A | 11/1996 | Errico et al. |
| 5,582,186 A | 12/1996 | Wiegand |
| 5,582,189 A | 12/1996 | Pannozzo |
| 5,590,271 A | 12/1996 | Klinker |
| 5,640,200 A | 6/1997 | Michael |
| 5,643,263 A | 7/1997 | Simonson |
| 5,683,392 A | 11/1997 | Richelsoph et al. |
| 5,688,274 A | 11/1997 | Errico et al. |
| 5,690,630 A | 11/1997 | Errico et al. |
| 5,707,643 A | 1/1998 | Ogura et al. |
| 5,715,334 A | 2/1998 | Peters |
| 5,725,527 A | 3/1998 | Biedermann et al. |
| 5,740,267 A | 4/1998 | Echerer et al. |
| 5,741,255 A | 4/1998 | Krag et al. |
| 5,748,703 A | 5/1998 | Cosman |
| 5,755,675 A | 5/1998 | Sihvonen |
| 5,772,592 A | 6/1998 | Cheng et al. |
| 5,772,595 A | 6/1998 | Votruba et al. |
| 5,784,431 A | 7/1998 | Kalend et al. |
| 5,797,911 A | 8/1998 | Sherman et al. |
| 5,810,006 A | 9/1998 | Votruba et al. |
| 5,813,406 A | 9/1998 | Kramer et al. |
| 5,824,072 A | 10/1998 | Wong |
| 5,838,759 A | 11/1998 | Armistead |
| 5,863,293 A | 1/1999 | Richelsoph |
| 5,879,350 A | 3/1999 | Sherman et al. |
| 5,880,976 A | 3/1999 | DiGioia, III et al. |
| 5,885,285 A | 3/1999 | Simonson |
| 5,891,060 A | 4/1999 | McGregor et al. |
| 5,891,145 A | 4/1999 | Morrison et al. |
| 5,899,859 A | 5/1999 | Votruba et al. |
| 5,931,781 A | 8/1999 | Boer |
| 5,954,674 A | 9/1999 | Fuhr |
| 5,964,760 A | 10/1999 | Richelsoph |
| 6,002,959 A | 12/1999 | Steiger et al. |
| 6,155,993 A | 12/2000 | Scott |
| 6,298,259 B1 | 10/2001 | Kucharczyk et al. |
| 6,428,490 B1 | 8/2002 | Kramer et al. |
| 6,432,053 B1 | 8/2002 | Fecht et al. |
| 6,434,264 B1 | 8/2002 | Asar |
| 6,497,672 B2 | 12/2002 | Kramer |
| 6,544,186 B1 | 4/2003 | Shelby et al. |
| 6,560,476 B1 | 5/2003 | Pelletier et al. |
| 6,726,691 B2 | 4/2004 | Osorio et al. |
| 6,755,839 B2 | 6/2004 | Hoeck et al. |
| 6,866,643 B2 | 3/2005 | Kramer |
| 6,890,312 B1 | 5/2005 | Priester et al. |
| 6,907,280 B2 | 6/2005 | Becerra et al. |
| 6,963,768 B2 | 11/2005 | Ho et al. |
| 6,990,368 B2 | 1/2006 | Simon et al. |
| 7,000,271 B2 | 2/2006 | Varadharajulu |
| 7,153,307 B2 | 12/2006 | Scribner et al. |
| 7,194,120 B2* | 3/2007 | Wicker .............. G06T 7/004 382/128 |
| 7,235,076 B2* | 6/2007 | Pacheco .......... A61B 17/1757 606/53 |
| 7,241,303 B2 | 7/2007 | Reiss et al. |
| 7,266,406 B2 | 9/2007 | Kroeckel |
| 7,300,441 B2 | 11/2007 | Haid et al. |
| 7,338,526 B2 | 3/2008 | Steinberg |
| 7,502,641 B2 | 3/2009 | Breen |
| 7,567,834 B2 | 7/2009 | Clayton et al. |
| 7,679,971 B1 | 3/2010 | Yu |
| 7,780,703 B2 | 8/2010 | Yuan et al. |
| 7,799,077 B2 | 9/2010 | Lang et al. |
| 7,835,778 B2 | 11/2010 | Foley et al. |
| 7,837,635 B2 | 11/2010 | Lissek et al. |
| 7,881,767 B2 | 2/2011 | Strommer et al. |
| 7,974,677 B2 | 7/2011 | Mire et al. |
| 8,394,144 B2 | 3/2013 | Zehavi et al. |
| 8,777,878 B2 | 7/2014 | Deitz |
| 8,876,830 B2 | 11/2014 | Hodorek et al. |
| 8,906,027 B2 | 12/2014 | Roche |
| 9,023,050 B2 | 5/2015 | Lang et al. |
| 2002/0120272 A1 | 8/2002 | Yuan et al. |
| 2003/0073901 A1* | 4/2003 | Simon ................ A61B 34/20 600/424 |
| 2003/0081837 A1 | 5/2003 | Williame et al. |
| 2003/0086596 A1 | 5/2003 | Hipp et al. |
| 2003/0220648 A1 | 11/2003 | Osorio et al. |
| 2003/0225327 A1 | 12/2003 | Willen et al. |
| 2004/0010260 A1 | 1/2004 | Scribner et al. |
| 2004/0098803 A1 | 5/2004 | Schindler |
| 2004/0141591 A1 | 7/2004 | Izuhara |
| 2004/0172145 A1 | 9/2004 | Varadharajulu |
| 2004/0225296 A1 | 11/2004 | Reiss et al. |

(56) References Cited

U.S. PATENT DOCUMENTS

| | | | |
|---|---|---|---|
| 2005/0107681 A1 | 5/2005 | Griffiths | |
| 2005/0148948 A1 | 7/2005 | Caputa | |
| 2005/0149050 A1* | 7/2005 | Stifter | A61B 34/20 606/102 |
| 2005/0187459 A1 | 8/2005 | Trequattrini et al. | |
| 2005/0222505 A1 | 10/2005 | Damadian et al. | |
| 2005/0240193 A1 | 10/2005 | Layne et al. | |
| 2005/0259794 A1 | 11/2005 | Breen | |
| 2006/0020196 A1 | 1/2006 | Elias | |
| 2006/0149136 A1 | 7/2006 | Seto et al. | |
| 2006/0185091 A1 | 8/2006 | Jackson | |
| 2006/0264952 A1 | 11/2006 | Nelson et al. | |
| 2007/0129634 A1 | 6/2007 | Hickey et al. | |
| 2007/0287900 A1 | 12/2007 | Breen et al. | |
| 2008/0009773 A1* | 1/2008 | Harrison | A61B 5/107 600/595 |
| 2008/0039867 A1 | 2/2008 | Feussner et al. | |
| 2008/0103601 A1* | 5/2008 | Biro | A61F 2/44 623/17.16 |
| 2008/0125678 A1 | 5/2008 | Breen | |
| 2008/0161680 A1* | 7/2008 | von Jako | A61B 5/06 600/424 |
| 2009/0089034 A1* | 4/2009 | Penney | A61B 90/36 703/11 |
| 2009/0099481 A1 | 4/2009 | Deitz | |
| 2009/0253095 A1 | 10/2009 | Salcedo et al. | |
| 2009/0285466 A1* | 11/2009 | Hipp | G06T 7/0014 382/131 |
| 2010/0174673 A1* | 7/2010 | Skalli | G06T 7/0065 706/50 |
| 2010/0191088 A1 | 7/2010 | Anderson et al. | |
| 2010/0249534 A1 | 9/2010 | Pierce et al. | |
| 2011/0054851 A1 | 3/2011 | Heller et al. | |
| 2012/0143090 A1* | 6/2012 | Hay | A61B 6/505 600/587 |
| 2012/0172700 A1* | 7/2012 | Krishnan | A61B 6/032 600/407 |
| 2012/0321168 A1 | 12/2012 | Deitz | |
| 2013/0060146 A1* | 3/2013 | Yang | A61B 34/20 600/476 |
| 2013/0202179 A1* | 8/2013 | Illes | A61B 5/1075 382/132 |
| 2013/0203031 A1 | 8/2013 | McKinnon et al. | |

FOREIGN PATENT DOCUMENTS

| | | |
|---|---|---|
| EP | 804032 A2 | 10/1997 |
| EP | 1123686 A2 | 8/2001 |
| EP | 1219240 A2 | 7/2002 |
| EP | 1519681 B1 | 11/2006 |
| JP | 07284020 A2 | 10/1995 |
| WO | 2005007217 A2 | 1/2005 |
| WO | 2011038236 A2 | 6/2011 |
| WO | 2012082615 A2 | 6/2012 |

OTHER PUBLICATIONS

Breen, et al. Lumbar spine motion palpation compared with objective intervertebral motion analysis: preliminary findings. Euro. J. Chiro. 50: 27-32 (2002).

Breen, et al. Spine kinematics: a digital videofluoroscopic technique, J. Biomed. Engr. 11: 224-8 (1989).

Bryant. Method for determining vertebral body positions in the sagittal plane using skin markers. Spine 14(3): 258-65 (1989).

Carragee, et al. Low-pressure positive Discography in subjects asymptomatic of significant low back pain illness. Spine. 31(5): 505-509 (2006).

Cholewicki, et al. Method for measuring vertebral kinematics from videofluoroscopy. Clinical Biomechanics 6: 73-8 (1991).

Cholewicki, et al. Lumbar posterior ligament involvement during extremely heavy lifts estimated from fluoroscopic measurements. J. Biomechanics 25(1): 17-28 (1992).

Esses, et al. Kinematic evaluation of lumbar fusion techniques. Spine 21(6): 676-84 (1996).

Fujiwara, et al. The relationship between disc degeneration, facet joint osteoarthritis, and stability of the degenerative lumbar spine. J. Spinal Disorders 13: 444-50 (2000).

Harada, et al. Cineradiographic motion analysis of normal lumbar spine during forward and backward flexion. Spine 25: 1932-7 (2000).

Johnsson, et al. Mobility of the lower lumbar spine after posterolateral fusion determined by roentgen stereophotogrammetric analysis. Spine 15: 347-50 (1990).

Jones, Cervical spine cineradiography after traffic accidents. Archives of Surgery 85: 974-81 (1962).

Kaigle, et al. Muscular and kinematic behavior of the lumbar spine during flexion-extension. Journal of Spinal Disorders. 11(2): 163-174 (1998).

Kleissen, et al., "Simultaneous Measurement of Surface EMG and Movements for Clinical USE" Med. Biol. Eng. Comp. 27( 3): 291-97 (1989).

Kondracki, Digital Videofluoroscopy, Manual Therapy 1, 146-48 (1996).

Lariviere, et al. A triaxial dynamometer to monitor lateral bending and axial rotation moments during static trunk extension efforts. Clin Biomech 16(1):80-3 (2001).

Lawrence, Disc degeneration. Its frequency and relationship to symptoms. Annals of Rheumatic Diseases 28:121-38 (1969).

Lee et al. Development and validation of a new technique for assessing lumbar spine motion, Spine 27(8): E215-20 (2002).

McGregor et al. Spinal motion in lumbar degenerative disc disease. J. Joint Surg (Br). 80-B: 1009-1013 (1998).

Medical Device & Surgery Technology Week, "Medical Devices; Release of surgical navigation software for knee implant system announced", Mar. 27, 2005:238, ISSN: 15371409. http://search.proquest.com/professional/docview/206901375?accountid=157282.

Medical Devices & Surgical Technology Week, "Orthopedics; Computer aided 'tools' to usher in next surgical revolution", Mar. 17, 2002; ISSN: 15371409. http://search.proquest.com/professional/docview206902428? accountid=17282.

Quick, et al. Real-Time MRI of Joint Movement with True FISP, J. Mag. Res. Imaging 15(6):710-15 (2002).

Schlenzka, D. et al., "Computer-assisted spine surgery", Eur Spine J (2000) 9 (Suppl 1):S57-S64.

Stokes, et al. Trunk muscular activation patterns and responses to transient force perturbation in persons with self-reported low back pain. Eur Spine J. 15:658-667 (2006).

Takayanagi, et al. Using cineradiography for continuous dynamic-motion analysis of the lumbar spine. Spine 26(17): 1858-1865 (2001).

Teyhen, et al., A New Technique for Digital Fluoriscopic Video Assessment of Sagittal Plane Lumbar Spine Motion, Spine vol. 30(14), pp. E406-E413 (2005).

Zheng, et al. Automatic Lumbar Vertebrae Segmentation in Fluoroscopic Images via Optimised Concurrent Hough Transform, 23rd Annual International Conf of IEEE Engineering in Med and Biology (2001).

\* cited by examiner

| | FUSION DECISION FACTORS: BLANKET STATEMENTS EACH DR. IS COMFORTABLE WITH | | | |
|---|---|---|---|---|
| | CONSIDER DOING FUSION FOR GENERAL CANDIDATE | CONSIDER FUSION WITH DECOMPRESSION OR DISCECTOMY | CONSIDER DOING FUSION FOR DISC ARTHROPLASTY CANDIDATE | CONSIDER DOING FUSION FOR DYNAMIC FUSION CANDIDATE |
| | (+) (−) | (+) (−) | (+) (−) | (+) (−) |
| INDEX LEVEL<br>PARADOXICAL<br>IMMOBILE<br>STIFF<br>NORMAL<br>HYP-ROT<br>HYP-TRANS<br>LAXITY<br>SLIP<br>% CONT HIGH<br>% CONT LOW | ☐ ☐ ☑ ☐ ☐ ☐ ☐ ☑ ☐<br>☐ ☐ ☐ ☑ ☐ ☐ ☐ ☐ ☑ ☐ | ☑ ☐ ☐ ☐ ☑ ☐ ☑ ☑ ☐ ☑<br>☐ ☐ ☑ ☑ ☐ ☐ ☐ ☐ ☐ ☐ | ☑ ☑ ☐ ☐ ☐ ☐ ☐ ☐ ☐ ☐<br>☐ ☐ ☐ ☑ ☐ ☐ ☐ ☐ ☑ ☐ | ☑ ☐ ☐ ☐ ☐ ☐ ☐ ☐ ☑ ☐<br>☐ ☐ ☑ ☑ ☐ ☐ ☐ ☐ ☐ ☑ |
| ADD ADJ. LEVEL?<br>PARADOXICAL<br>IMMOBILE<br>STIFF<br>NORMAL<br>HYP-ROT<br>HYP-TRANS<br>LAXITY<br>SLIP<br>% CONT HIGH<br>% CONT LOW | ☑ ☐ ☐ ☑ ☐ ☐ ☐ ☐ ☑<br>☐ ☐ ☐ ☑ ☐ ☐ ☐ ☐ ☑ ☐ | ☑ ☐ ☐ ☐ ☑ ☐ ☑ ☐ ☐ ☐<br>☐ ☐ ☐ ☑ ☐ ☐ ☐ ☐ ☐ ☐ | | |

Figure 7b

| | FUSION DECISION FACTORS: BLANKET STATEMENTS EACH DR. IS COMFORTABLE WITH | | | | | | | |
|---|---|---|---|---|---|---|---|---|
| | CONSIDER DOING FUSION FOR GENERAL CANDIDATE | | CONSIDER FUSION WITH DECOMPRESSION OR DISCECTOMY | | CONSIDER DOING FUSION FOR DISC ARTHROPLASTY CANDIDATE | | CONSIDER DOING FUSION FOR DYNAMIC FUSION CANDIDATE | |
| | (+) | (−) | (+) | (−) | (+) | (−) | (+) | (−) |
| ANY NON-OP LEVEL | | | | | | | | |
| PARADOXICAL | ☐ | ☐ | ☐ | ☐ | ☐ | ☐ | ☐ | ☐ |
| IMMOBILE | ☐ | ☐ | ☐ | ☐ | ☐ | ☐ | ☐ | ☐ |
| STIFF | ☐ | ☐ | ☐ | ☐ | ☐ | ☐ | ☐ | ☐ |
| NORMAL | ☐ | ☒ | ☐ | ☐ | ☐ | ☒ | ☐ | ☐ |
| HYP-ROT | ☐ | ☒ | ☐ | ☐ | ☐ | ☐ | ☐ | ☐ |
| HYP-TRANS | ☐ | ☐ | ☐ | ☐ | ☐ | ☒ | ☐ | ☐ |
| LAXITY | ☐ | ☒ | ☐ | ☐ | ☐ | ☐ | ☐ | ☐ |
| SLIP | ☐ | ☐ | ☐ | ☐ | ☐ | ☐ | ☐ | ☐ |
| % CONT HIGH | | | | | | | | |
| % CONT LOW | | | | | | | | |
| OVERALL L1-S1 REGION | | | | | | | | |
| STIFF | ☐ | ☒ | ☐ | ☒ | ☐ | ☒ | ☒ | ☐ |
| NORMAL | ☐ | ☐ | ☒ | ☐ | ☒ | ☐ | ☐ | ☐ |
| HYP-ROT | ☒ | ☐ | ☐ | ☐ | ☐ | ☐ | ☐ | ☒ |

|  | INDEX LEVEL | | ADJACENT LEVEL | |
|---|---|---|---|---|
|  | GOOD | BAD | GOOD | BAD |
| GENERAL FUSION | • IMMOBILE<br>• LOW %<br>  CONTRIBUTION | • NORMAL<br>• HIGH %<br>  CONTRIBUTION | • NORMAL | • PARADOXICAL<br>• IMMOBILE<br>• LAX<br>• HYPER-ROT<br>• HYPER-TRANS |
| FUSION WITH DECOMPRESSION? | • PARADOXICAL<br>• IMMOBILE<br>• LAX<br>• HYPER-ROT<br>• HYPER-TRANS | • IMMOBILE<br>• STIFF | • NORMAL | • PARADOXICAL<br>• IMMOBILE<br>• LAX<br>• HYPER-ROT<br>• HYPER-TRANS |
| *CONSIDERATION OF FUSION ALTERNATIVES?* | | | | |
| FUSION VS. DISC ARTHROPLASTY? | • IMMOBILE<br>• STIFF | • NORMAL<br>• LOW %<br>  CONTRIBUTION | • HIGH %<br>  CONTRIBUTION | |
| FUSION VS. DYNAMIC FUSION? | • STIFF | • IMMOBILE | | |

| NAVIGATION TARGET | BIOMECHANICAL GOAL | CLINICAL BENEFIT |
|---|---|---|
| LOCATION & ORIENTATION OF THE SUPERIOR AND INFERIOR ENDPLATES OF A FUSION CONSTRUCT | ENSURE THAT ADJACENT LEVEL CORS ARE AS CLOSE TO 'NORMAL' AS POSSIBLE | AVOID ABNORMAL FACET LOADING (IF COR IS TOO ANTERIOR), OFF-LOADING (IF TOO POSTERIOR), AND LEFT/RIGHT IMBALANCES |
| PLACEMENT OF INTERBODY AND MOTION PRESERVING DEVICES ON VERTEBRAL ENDPLATE | ENSURE DEVICE OVERLAPS WITH COR OF THE JOINT, ALIGNING FORCES THROUGH THE DEVICE AND AVOIDING PROBLEMATIC MOMENT ARMS | • TAKE ADVANTAGE OF WOLF'S LAW TO OPTIMIZE BONE IN-GROWTH<br>• REDUCE STRESSING MOMENT ARMS TO AVOID FAILURE OF CONSTRUCT |

Figure 12

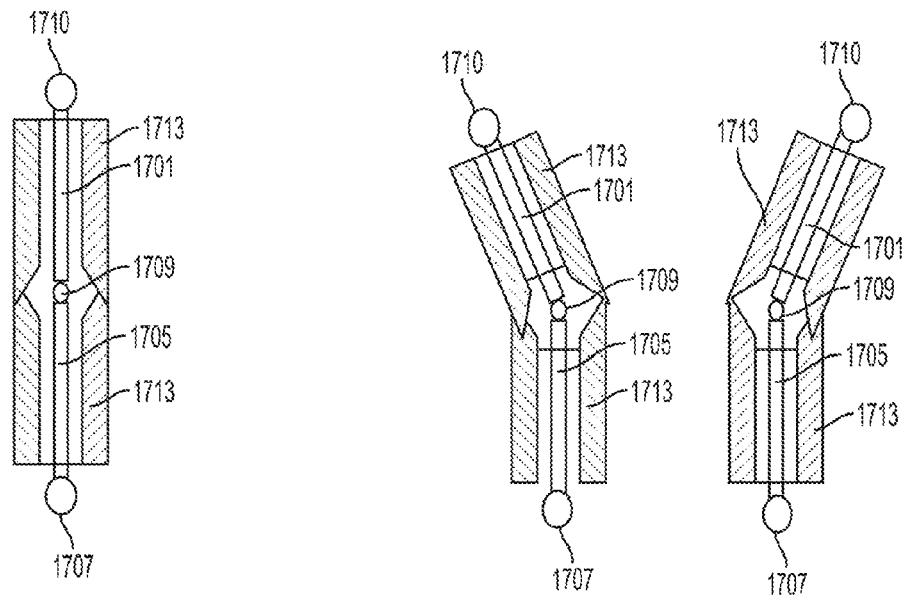
Figure 17A
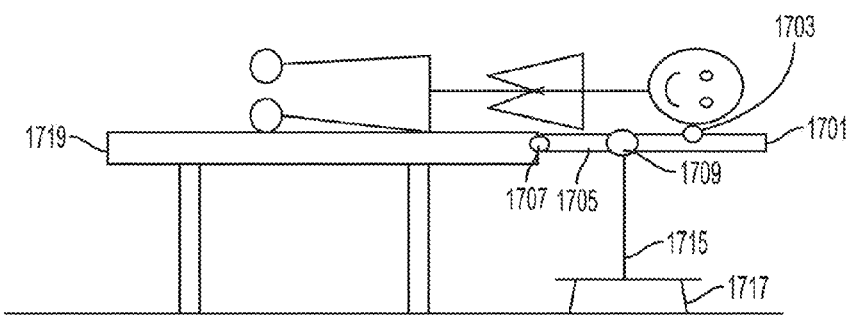
Figure 17B

METHODS, SYSTEMS AND DEVICES FOR SPINAL SURGERY POSITION OPTIMIZATION

CROSS-REFERENCE

This application is a continuation of application Ser. No. 13/882,022, filed Dec. 12, 2011 which is the national stage of PCT/US2011/64404 filed Dec. 12, 2011, which claims the benefit of U.S. Provisional Application Nos. 61/451,548 filed Mar. 10, 2011, entitled Medical Imaging System Mounted and Movable Within a Vertical Plane for Imaging Moving Objects; 61/422,283, filed Dec. 13, 2010, entitled Methods, Systems and Devices for a Clinical Data Reporting Software System, 61/444,265 filed Feb. 18, 2011, entitled Methods, Systems and Devices for A Clinical Data Reporting And Surgical Navigation, 61/453,236 filed Mar. 16, 2011, entitled Methods, Systems and Devices for a Clinical Data Reporting Software System, 61/454,601 filed Mar. 21, 2011, entitled Methods, Systems and Devices for a Clinical Data Reporting Software System and Product Design Tools, and 61/499,272 filed Jun. 21, 2011, entitled Methods, Systems and Devices for a Clinical Data Reporting and Surgical Navigation which applications are incorporated herein by reference.

BACKGROUND OF THE INVENTION

One of the most prevalent joint problems is back pain, particularly in the "small of the back" or lumbosacral (L4-S1) region. In many cases, the pain severely limits a person's functional ability and quality of life. Such pain can result from a variety of spinal pathologies. Through disease or injury, the vertebral bodies, intervertebral discs, laminae, spinous process, articular processes, or facets of one or more spinal vertebrae can become damaged, such that the vertebrae no longer articulate or properly align with each other. This can result in an undesired anatomy, loss of mobility, and pain or discomfort. Duke University Medical Center researchers found that patients suffering from back pain in the United States consume more than $90 billion annually in health care expenses, with approximately $26 billion being directly attributable to treatment. Additionally, there is a substantial impact on the productivity of workers as a result of lost work days. Similar trends have also been observed in the United Kingdom and other countries.

As part of the diagnostic process of determining the cause of pain coming from a joint such as the lumbar spine, health care providers rely on an understanding of joint anatomy and mechanics when evaluating a subject's suspected joint problem and/or biomechanical performance issue. Currently available orthopedic diagnostic methods are capable of detecting a limited number of specific and treatable defects. These techniques include X-Rays, MRI, discography, and physical exams of the patient. In addition, spinal kinematic studies such as flexion/extension X-rays are used to specifically detect whether or not a joint has dysfunctional motion. These methods have become widely available and broadly adopted into the practice of treating joint problems and addressing joint performance issues.

U.S. Patent No. US 2004-0172145 A1 discloses a tilting table capable of some movement to keep an iso-center at a fixed position. U.S. Patent Publication No.: US 2006-0185091 A1 describes a multi-articulated tilting table which positions and supports a subject during examination and treatment. U.S. Pat. Publication No. US 2005-0259794 A1 to Breen discloses a device for controlling joint motion and minimizing the effects of muscle involvement in the joint motion being studied. See also U.S. Pat. No. 7,502,641. This device minimizes variability among joint motion measurements across wide populations of subjects. As a result, comparative analyses of such measurements can be performed to determine statistical differences between the motion of "normal" and "unhealthy" subjects which in turn can provide a basis for determining the statistical confidence with which any given subject could be considered "normal" or "unhealthy" based solely on joint motion measurements. US 2009/0099481 A1 to Deitz for Devices, Systems and Methods for Measuring and Evaluating the Motion and Function of Joints and Associated Muscles discloses an apparatus configured to cause and control joint motion of a patient.

New approaches that involve the use of patient positioning devices during imaging discussed above, coupled with the use of imaging modalities that afford for moving-video type images (such as fluoroscopy) and automated computer image processing, have created new clinical diagnostic capabilities. These capabilities include the ability to produce low variability, quantitative measurements of the relative motion between anatomical structures in mammals, and in particular the ability to measure inter-vertebral kinematics in live human subjects. These new capabilities have been validated in clinical studies to significantly outperform older methods, such as flexion/extension X-rays, in determining whether or not a human spine joint has dysfunctional motion. With the development of these new systems for assessing inter-vertebral kinematics, there arises the need for components to enable a number of clinical applications of this newly-available diagnostic data.

One need is for new ways of viewing this new type of kinematic data. Another need is for the ability to leverage this data to improve upon the tools that users have in providing therapy to patients. Yet another need is to be able to generate measurement system results for anatomy that is typically hard or impossible to image, such as anatomy that does not stay fixed in space during operation, such as a knee (as opposed to a lumbar spine, which can be easily imaged with a fixed imaging device).

SUMMARY OF THE INVENTION

Three components to the system are proposed, each component is adapted and configured to work with a measurement system or device for producing or obtaining measurements of a relative motion of anatomical structures of mammals. The measurement system in this case would be comprised of, for example, an apparatus for imaging a target joint through a prescribed range of motion to obtain one or more images, and a process or device for deriving quantitative measurement output data from the images. The components of the present disclosure include: (1) a software device having a user interface which delivers data from the measurement system; (2) an apparatus and method for utilizing measurement output of the measurement system for therapeutic and surgical applications such as surgical navigation and patient positioning during a therapeutic procedure; and (3) an apparatus providing input image data for the measurement system that assists with imaging during joint operation to afford for the imaging of joints connecting anatomical regions that are in motion during operation. The user is typically a healthcare provider or clinician.

The first of these three components, the clinical data reporting software interface, is an algorithm encoded in computer-readable media which delivers to a user interface at least one measurement output from the measurement system communicate through the process of initialization by a user, interpretation of results from the measurement system, and comparison with aggregated data contained in the computer readable media. The software interface is configured to operate in a communications network, and with one or more input and output devices.

The clinical data reporting software interface allows the user to initialize the system once prior to or during a first use of the software interface to define, for example, a list of one or more procedures of interest, one or more associated risks, and one or more risk mitigation factors associated with each procedure. The initialization information can be updated as often as desired, and/or can be dynamically updated by communication with an service provided. These risk and risk mitigation factors relate to the appropriateness of a particular procedures in view of a specific patient's presentations. The combination of risk and risk mitigation factors are definable as specific alerts in the reporting system that can be presented to the user for consideration of changes to planned procedures for each patient based on that patient's specific measurement system testing results.

The clinical data reporting software interface integrates user preferences for procedures of interest along with associated risk factors and risk mitigation factors to facilitate interpretation of patient specific results for specific kinematic dysfunctions, at each spine level. Threshold limits for quantitatively detecting kinematic dysfunctions can be set and changed interactively by the user.

The clinical data reporting software interface provides a process and mechanism for collecting additional data on each subject to include: demographic, height/weight/other physical measurements, subject history, symptoms, co-morbidities, neurologic exam results, prior procedures performed and related outcome, and others; as well as a process and device for transmitting this additional data to an aggregated database.

The clinical data reporting software interface provides a process and device for collecting aggregated data from all subjects tested, creating a database that can be used for consideration and comparison of outcomes for subjects matched based on: 1) kinematic presentation, 2) additional data collected, and 3) procedure being considered. User can view potential clinical outcomes of procedure being considered by querying aggregated database.

The clinical data reporting software interface interprets kinematic results of subjects that were tested in a standing or lying down position, which allows for isolating the muscle or load contribution, and additionally allowing for the use of this data within a computer model of spine biomechanics that can further isolate the potential muscular and soft tissue causes of any functional problems.

The surgical navigation and patient positioning system is an apparatus and method for utilizing measurement output of the measurement system during therapeutic procedures. It comprises a communications network, communication medium, input and output devices, computing application and software application that communicate and compute data through the process of acquisition of data from the measurement system, processing of data to determine appropriate target geometric and spatial parameters, communicating this data to a surgical navigation system and/or a patient positioning device (such as an intra-operative patient positioning device).

The surgical navigation and patient positioning system provides a mechanism to incorporate kinematic data into systems used by users during therapeutic procedures, specifically surgical navigation and surgical patient positioning systems. In the case of surgical navigation, an apparatus and method are provided for determining the optimal geometry for a surgical construct; such as determining the optimal spatial relationships between and among an inter-body device, posterior rods and screws, and two vertebral endplates for spinal fusion surgical construct. Once determined, the data describing this optimal geometry is then communicated to a surgical navigation system and incorporated into the system's targeting module, so that the surgical navigation system can be used to assist the surgeon in achieving optimal geometry for the surgical construct. In the case of patient positioning (such as intra-operative patient positioning), an apparatus and method are provided for determining and achieving the optimal positioning of the patient on the procedure table. Once determined, the data describing this optimal positioning of the patient is then communicated to a surgical patient positioning system and incorporated into the position control system so that the optimal patient position can be achieved during surgery. The control system can additionally be in communication with additional patient data collection systems to provide real time feedback as to the effect of patient positioning changes on the position, orientation, and motion of the anatomy of interest, for the purpose of allowing the control system to achieve the target anatomical geometry and orientation by adjustments made to the surgical patient positioning system.

The imaging system is adaptable to be moveable within a vertical plane and is an apparatus providing input image data for the measurement system that assists with imaging during joint operation. It consists of a medical imaging system mounted to a free floating, ballasted vertical plane, so that the medical imaging system can be moved to keep joint anatomy within a moving field of view, such as keeping a knee in a field of view as a live human testing subject is walking. It incorporates motion recording sensors positionable with respect to an image intensifier system motion, with attachment mechanisms to engage the medical imaging system or the recording sensors to piece of human anatomy. It may additionally incorporate actuators capable of providing the motive force to affect a repositioning of the medical imaging system.

Having an imaging system moveable within a vertical plane is ideal for use with joints that connect two anatomical regions that both move, such as the human knee that connects the tibia/fibula to the femur, both of which are in motion during operation of the knee. This is in contrast to joints where one of the two anatomical regions connected by the joint stays relatively fixed, such as the torso for shoulder rotation, or the pelvis for lumbar spine rotation, and therefore can be imaged with a fixed imaging system such that the joint stays in within the field of imaging during operation. When both of the anatomical regions connected by a joint are in motion, it can be impossible to keep that joint within a field of view unless the imaging system is moving as well, which is an operational objective of the imaging system moveable within a vertical plane.

For all three of the components included in the present disclosure, the inputs, information and reports can be transmitted through either a direct wire-based electronic connection between the two or more components, or through a wireless connection, and can be of the type that is derived from computer programming or from operator, user or subject input, or from a combination of computer programmed information plus operator, user and/or subject input. Those skilled in the art will appreciate that the system described herein can be applied or incorporated into any communications network, communication medium, input and output devices and computing application available now and what will be available in the future.

An aspect of the disclosure is directed to a method for computer-assisted analysis of kinematic data. A method comprising, for example, encoding a kinematic evaluation algorithm as one or more decision trees, each decision tree further comprising, one or more decision points comprising one or more questions; and one or more termination points, providing one or more images for a patient from an imaging system; initiating an evaluation by identifying one or more proposed procedures for the patient; evaluating the proposed procedure applied to the one or more images from the imaging system according to the algorithm; comparing the evaluation of the proposed procedure to a user profile; and providing a summary of one or more alerts for the one or more proposed procedures based on the user profile and the one or more patient images. Additionally, the method can be performed on a communication network. In some aspects, the method further comprises the steps of: creating a user profile prior to the step of providing one or more images from an imaging system wherein the step of creating further comprises identifying one or more procedures of interest for the user, creating one or more alerts for the one or more procedures of interest based on a user preference, wherein the alerts include one or more kinematic risk factors and one or more kinematic mitigation factors. Additionally, the one or more alerts can be based on one or more threshold limits set by the user, either during the initiation process or during a later adjustment. The method is adaptable such that the user an user change the one or more threshold limits at any time, including during evaluation of a particular patient's data. Typically, a summary is provided to the user by a results viewer. In some aspects, the additional steps of comparing the evaluation of the proposed procedure to the updated one or more threshold limits and providing an updated summary of one or more alerts for the one or more proposed procedures is also contemplated. Additionally, one or more alerts can be allocated a priority and, in at least some configurations, the one or more alerts can be presented to the user in a sort based on the allocated priority. Additionally, risk mitigation factors are categorizable as at least one or more of good, bad, and neutral. Moreover, in at least some aspects, the summary is displayed on an electronic device screen and further wherein the summary is displayed with one or more of each of videos, images, and tables. Additionally, the step of evaluating can further comprise evaluating one or more patient specific parameters. In at least some situations, the one or more patient specific parameters is one or more parameter selected from the group comprising: demographics, height, weight, physical measurements, health history, symptoms, neurological exam results, co-morbidities.

Still another aspect of the disclosure is directed to a method for computer-assisted analysis of kinematic data. The computer-assisted method comprises, for example: aggregating kinematic data from two or more patients into a database; encoding a kinematic evaluation algorithm as one or more decision trees, each decision tree further comprising, one or more decision points comprising one or more questions; and one or more termination points, providing one or more images for a patient from an imaging system according to the algorithm; initiating an evaluation by identifying one or more proposed procedures for the patient; evaluating the proposed procedure applied to the one or more images from the imaging system and the database of aggregated data; comparing the evaluation of the proposed procedure to a user profile; and providing a summary of one or more alerts for the one or more proposed procedures based on the user profile and the one or more patient images. Additionally, the method can be performed on a communication network. In some aspects, the method further comprises the steps of: creating a user profile prior to the step of providing one or more images from an imaging system wherein the step of creating further comprises identifying one or more procedures of interest for the user, creating one or more alerts for the one or more procedures of interest based on a user preference, wherein the alerts include one or more kinematic risk factors and one or more kinematic mitigation factors. Additionally, the one or more alerts can be based on one or more threshold limits set by the user, either during the initiation process or during a later adjustment. The method is adaptable such that the user an user change the one or more threshold limits at any time, including during evaluation of a particular patient's data. Typically, a summary is provided to the user by a results viewer. In some aspects, the additional steps of comparing the evaluation of the proposed procedure to the updated one or more threshold limits and providing an updated summary of one or more alerts for the one or more proposed procedures is also contemplated. Additionally, one or more alerts can be allocated a priority and, in at least some configurations, the one or more alerts can be presented to the user in a sort based on the allocated priority. Additionally, risk mitigation factors are categorizable as at least one or more of good, bad, and neutral. Moreover, in at least some aspects, the summary is displayed on an electronic device screen and further wherein the summary is displayed with one or more of each of videos, images, and tables. Additionally, the step of evaluating can further comprise evaluating one or more patient specific parameters. In at least some situations, the one or more patient specific parameters is one or more parameter selected from the group comprising: demographics, height, weight, physical measurements, health history, symptoms, neurological exam results, co-morbidities.

Yet another aspect of the disclosure is directed to a system for evaluating kinematic data received from a patient. The system comprises: an imaging system adapted to capture one or more images of a target joint from a patient; a modeler adapted to provide a model of a target biomechanical behavior for the target joint; a comparer adapted to compare the one or more images of the target joint with the computer implemented model and generate resulting image. The system can include a communication network through which various components of the system communicate. The system can further comprising one or more of a computer, a smart phone, and a tablet. Additionally, the system of claim can further include a database of kinematic data. The database of kinematic data can be from one or more patients. Additionally, a results viewer can be provided.

In still another aspect of the disclosure, a system for obtaining kinematic data from a patient is provided which comprises: an imaging system adapted to capture one or more images of a target joint from a patient; an apparatus for measuring joint motion comprising, a passive motion device adapted and configured to continuously move a joint of the subject through a range of motion, the passive motion device further comprising, a platform base, and a passive motion platform further comprising a static platform connected to an upper surface of the platform base, a movable platform connected to at least one of the static platform or an upper surface of the platform base, wherein the static platform is adjacent the movable platform wherein movement of the movable platform is achieved in operation by a motor in communication with the moveable platform, and an imaging device adapted and configured to image the joint of the subject during the motion of the passive motion device, a comparer adapted to compare the one or more images of the target joint with the computer implemented model. The system can include a communication network through which various components of the system communicate. The system can further comprising one or more of a computer, a smart phone, and a tablet. Additionally, the system of claim can further include a database of kinematic data. The database of kinematic data can be from one or more patients. Additionally, a results viewer can be provided.

Yet another aspect of the disclosure is directed to a surgical system comprising: an imaging system adapted to capture one or more images of a target joint from a patient; an apparatus for measuring joint motion comprising, a passive motion device adapted and configured to continuously move a joint of the subject through a range of motion, the passive motion device further comprising, a platform base, and a passive motion platform further comprising a static platform connected to an upper surface of the platform base, a movable platform connected to at least one of the static platform or an upper surface of the platform base, wherein the static platform is adjacent the movable platform wherein movement of the movable platform is achieved in operation by a motor in communication with the moveable platform, and an imaging device adapted and configured to image the joint of the subject during the motion of the passive motion device; and a device having a plurality of articulating arms having at least two articulation joints, the articulating arms being adapted to be inserted into an operative space and further adapted to controllably articulate inside the operative space, with at least three degrees of freedom of movement, at least one access port adapted to receive the articulating arms, and a controller adapted to control the articulation of the articulating arms inside the operative space to perform a surgical procedure. The system can include a communication network through which various components of the system communicate. The system can further comprising one or more of a computer, a smart phone, and a tablet. Additionally, the system of claim can further include a database of kinematic data. The database of kinematic data can be from one or more patients. Additionally, a results viewer can be provided.

An aspect of the disclosure is directed to a method for computer-assisted analysis of kinematic data. Methods comprise: encoding a kinematic evaluation algorithm as one or more decision trees, each decision tree further comprising, one or more decision points comprising one or more questions; and one or more termination points, providing one or more images for a patient from an imaging system; initiating an evaluation by identifying one or more proposed procedures for the patient; evaluating the proposed procedure applied to the one or more images from the imaging system according to the algorithm; comparing the evaluation of the proposed procedure to a user profile; and providing a summary of one or more alerts for the one or more proposed procedures based on the user profile and the one or more patient images. Additionally the method can be performed on a communication network, such as the Internet or an intranet using wired and wireless capability. Additional method steps can include, creating a user profile prior to the step of providing one or more images from an imaging system wherein the step of creating further comprises identifying one or more procedures of interest for the user, creating one or more alerts for the one or more procedures of interest based on a user preference, wherein the alerts include one or more kinematic risk factors and one or more kinematic mitigation factors. In at least some instances, one or more alerts can be issued based on one or more threshold limits set by the user. Users can also change the one or more threshold limits either at a mail profile (thus impacting all cases or all future cases evaluated) or for a specific case. Additionally, the summary is provided to the user by a results viewer. Additionally, the method can include comparing the evaluation of the proposed procedure to the updated one or more threshold limits and providing an updated summary of one or more alerts for the one or more proposed procedures. Moreover, the one or more alerts are allocated a priority and further wherein the one or more alerts are sorted based on the allocated priority. In some aspects, the risk mitigation factors are categorizable as at least one or more of good, bad, and neutral. Additionally, the summary is displayed on an electronic device screen and further wherein the summary is displayed with one or more of each of videos, images, and tables. The step of evaluating can further comprise evaluating one or more patient specific parameters. Suitable patient parameters include, for example, one or more parameter selected from the group comprising: demographics, height, weight, physical measurements, health history, symptoms, neurological exam results, co-morbidities.

Another aspect of the disclosure is directed to a method for computer-assisted analysis of kinematic data where the method comprises: aggregating kinematic data from two or more patients into a database; encoding a kinematic evaluation algorithm as one or more decision trees, each decision tree further comprising, one or more decision points comprising one or more questions; and one or more termination points, providing one or more images for a patient from an imaging system according to the algorithm; initiating an evaluation by identifying one or more proposed procedures for the patient; evaluating the proposed procedure applied to the one or more images from the imaging system and the database of aggregated data; comparing the evaluation of the proposed procedure to a user profile; and providing a summary of one or more alerts for the one or more proposed procedures based on the user profile and the one or more patient images. Additionally the method can be performed on a communication network, such as the Internet or an intranet using wired and wireless capability. Additional method steps can include, creating a user profile prior to the step of providing one or more images from an imaging system wherein the step of creating further comprises identifying one or more procedures of interest for the user, creating one or more alerts for the one or more procedures of interest based on a user preference, wherein the alerts include one or more kinematic risk factors and one or more kinematic mitigation factors. In at least some instances, one or more alerts can be issued based on one or more threshold limits set by the user. Users can also change the one or more threshold limits either at a mail profile (thus impacting all cases or all future cases evaluated) or for a specific case. Additionally, the summary is provided to the user by a results viewer. Additionally, the method can include comparing the evaluation of the proposed procedure to the updated one or more threshold limits and providing an updated summary of one or more alerts for the one or more proposed procedures. Moreover, the one or more alerts are allocated a priority and further wherein the one or more alerts are sorted based on the allocated priority. In some aspects, the risk mitigation factors are categorizable as at least one or more of good, bad, and neutral. Additionally, the summary is displayed on an electronic device screen and further wherein the summary is displayed with one or more of each of videos, images, and tables. The step of evaluating can further comprise evaluating one or more patient specific parameters. Suitable patient parameters include, for example, one or more parameter selected from the group comprising: demographics, height, weight, physical measurements, health history, symptoms, neurological exam results, co-morbidities.

Still another aspect of the disclosure is directed to a system for evaluating kinematic data from a patient. A suitable system comprises: an imaging system adapted to capture one or more images of a target joint from a patient; a modeler adapted to provide a model of a target biomechanical behavior for the target joint; a comparer adapted to compare the one or more images of the target joint with the computer implemented model and generate resulting image. The system can further be configured to operate on or in conjunction with a communication network, such as the Internet or an intranet using wired and wireless capability. Additionally, the system can employ one or more of a computer, a smart phone, and a tablet. Additionally, the system can create, access, and/or maintain a database of kinematic data. A results viewer can also be provided.

Yet another aspect of the disclosure is directed to a system for obtaining kinematic data from a patient wherein the system comprises: an imaging system adapted to capture one or more images of a target joint from a patient; an apparatus for measuring joint motion comprising a passive motion device adapted and configured to continuously move a joint of the subject through a range of motion, the passive motion device further comprising, a platform base, and a passive motion platform further comprising a static platform connected to an upper surface of the platform base, a movable platform connected to at least one of the static platform or an upper surface of the platform base, wherein the static platform is adjacent the movable platform wherein movement of the movable platform is achieved in operation by a motor in communication with the moveable platform, and an imaging device adapted and configured to image the joint of the subject during the motion of the passive motion device a comparer adapted to compare the one or more images of the target joint with the computer implemented model. The system can further be configured to operate on or in conjunction with a communication network, such as the Internet or an intranet using wired and wireless capability. Additionally, the system can employ one or more of a computer, a smart phone, and a tablet. Additionally, the system can create, access, and/or maintain a database of kinematic data. A results viewer can also be provided.

Another aspect of the disclosure is directed to a surgical system. The surgical system comprises, for example, an imaging system adapted to capture one or more images of a target joint from a patient; an apparatus for measuring joint motion comprising, a passive motion device adapted and configured to continuously move a joint of the subject through a range of motion, the passive motion device further comprising, a platform base, and a passive motion platform further comprising a static platform connected to an upper surface of the platform base, a movable platform connected to at least one of the static platform or an upper surface of the platform base, wherein the static platform is adjacent the movable platform wherein movement of the movable platform is achieved in operation by a motor in communication with the moveable platform, and an imaging device adapted and configured to image the joint of the subject during the motion of the passive motion device; and a device having a plurality of articulating arms having at least two articulation joints, the articulating arms being adapted to be inserted into an operative space and further adapted to controllably articulate inside the operative space, with at least three degrees of freedom of movement, at least one access port adapted to receive the articulating arms, and a controller adapted to control the articulation of the articulating arms inside the operative space to perform a surgical procedure. The surgical system can further be configured to operate on or in conjunction with a communication network, such as the Internet or an intranet using wired and wireless capability. Additionally, the surgical system can employ one or more of a computer, a smart phone, and a tablet. Additionally, the surgical system can create, access, and/or maintain a database of kinematic data. A results viewer can also be provided.

An additional aspect of the disclosure is directed to an imaging system comprising: a motion device for continuously moving a mammalian joint; an imaging device mounted to a free floating, ballasted vertical plane, wherein the imaging device is moveable relative to the motion device during use to maintain a target anatomy within a targeted field of view; and a connector adapted to connect the imaging device to the motion device such that the imaging device and motion device move together when activated. One or more actuators can also be provided that are in communication with the processing system and adapted to reposition the imaging device in response to the instruction. Additionally, a collimator can be included. In some configurations, the system comprises one or more motion sensors positionable on a patient and in communication with one or more of the imaging device and one or more recording sensors. In still other configurations, a processing system for processing information from the one or more motion sensors to generate an instruction is provided. Additionally, one or more actuators in communication with the processing system and adapted to reposition the imaging device and motion device in response to an instruction can be provided. In some configurations, the instruction is at least one of automatically generated, semi-automatically generated, or manually generated, or combinations thereof. Moreover, the connector can be a connection rod.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 7b and 7c illustrate pages a first and second page of a two-page example of one embodiment of the type of data collected as part of the initialization step that each user undergoes prior to using the clinical data reporting software interface;

FIG. 7d illustrates a screen shot of how alerts can be configured during the initialization process and then subsequently changed by the user using the clinical data reporting software interface;

FIG. 7e illustrates types of alerts that, for example, a spine surgeon may want to be warned about using the clinical data reporting software interface;

FIGS. 8b, 8c, and 8d are three screens shot that illustrate how a user of the clinical data reporting software would interact with the system to input data, view, and query the aggregated database. In FIG. 8b, a user interface is shown.

In FIG. 8c a method for inputting neurological exam results into the aggregated database is shown. FIG. 8d a method for inputting a patient's pain scores into the aggregated database, as well as functionality that enables a user to select among various outcomes assessments to be output, are shown.

FIG. 12 is a table illustrating ways in which functional targets could be clinically useful in a surgical navigation system, as enabled via the surgical navigation and patient positioning;

FIGS. 17A-B illustrate the functionality of a collimator device and a collimator in conjunction with a patient examination table suitable for use with this system.

DETAILED DESCRIPTION OF THE INVENTION

I. Anatomical Context

Figure 1A:
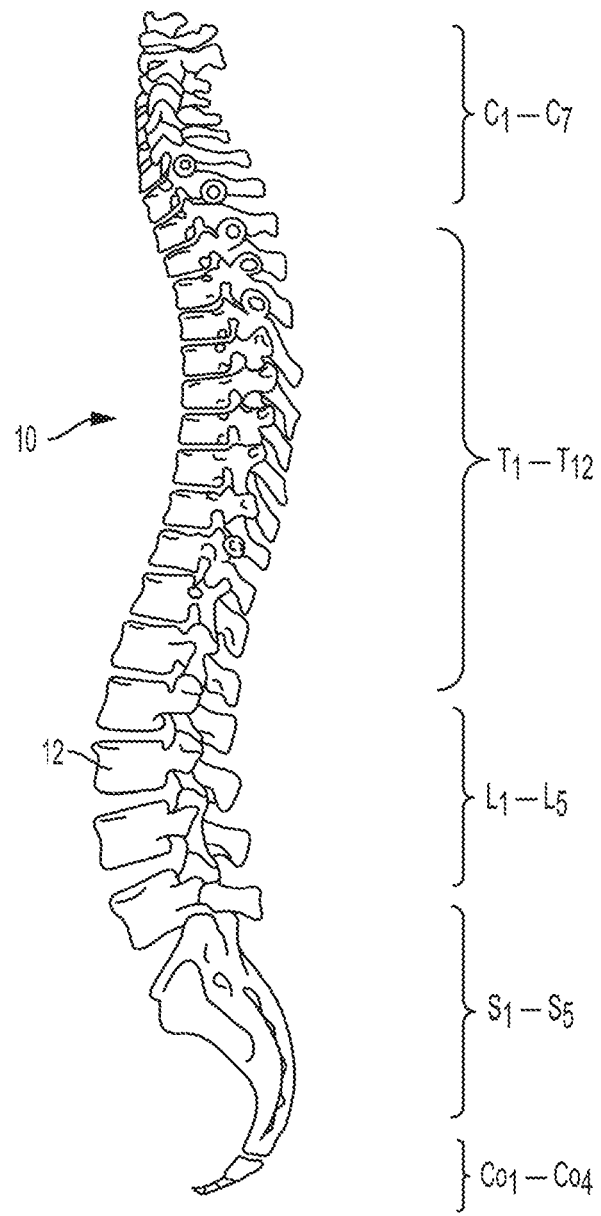
FIG. 1A is a lateral view of a normal human spinal column.

FIG. 1 illustrates the human spinal column 10 which is comprised of a series of thirty-three stacked vertebrae 12 divided into five regions. The cervical region includes seven vertebrae, known as C1-C7. The thoracic region includes twelve vertebrae, known as T1-T12. The lumbar region contains five vertebrae, known as L1-L5. The sacral region is comprised of five fused vertebrae, known as S1-S5, while the coccygeal region contains four fused vertebrae, known as Co1-Co4.

Figure 1B:
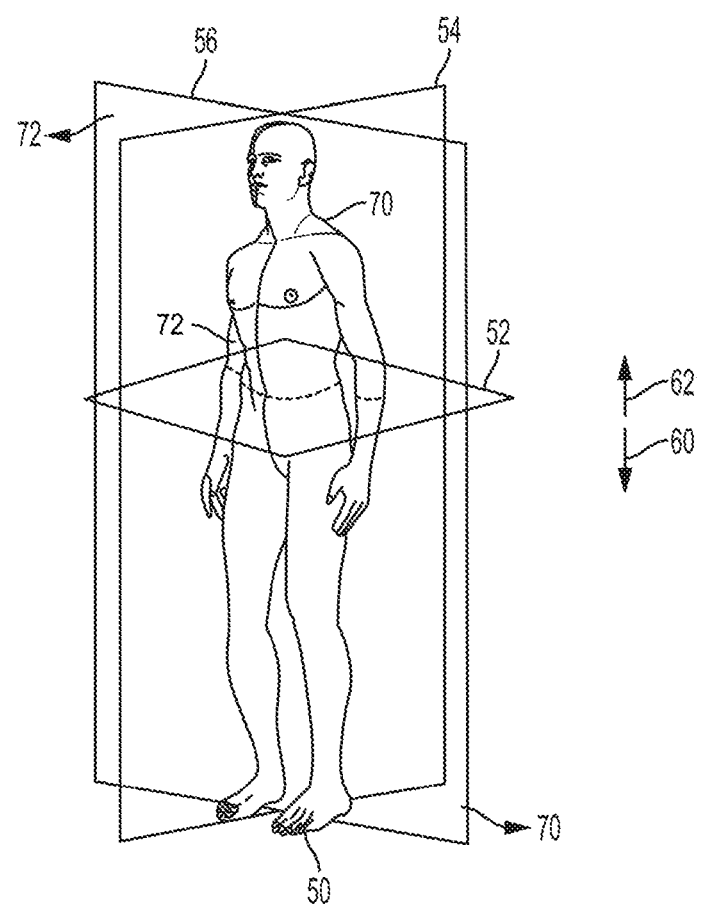
FIG. 1B is illustrates a human body with the planes of the body identified.

In order to understand the configurability, adaptability, and operational aspects of the systems, methods and devices disclosed herein, it is helpful to understand the anatomical references of the body 50 with respect to which the position and operation of the devices, and components thereof, are described. As shown in FIG. 1B, there are three anatomical planes generally used in anatomy to describe the human body and structure within the human body: the axial plane 52, the sagittal plane 54 and the coronal plane 56. Additionally, devices and the operation of devices and tools may be better understood with respect to the caudad 60 direction and/or the cephalad direction 62. Devices and tools can be positioned dorsally 70 (or posteriorly) such that the placement or operation of the device is toward the back or rear of the body. Alternatively, devices can be positioned ventrally 72 (or anteriorly) such that the placement or operation of the device is toward the front of the body. Various embodiments of the devices, systems and tools of the present disclosure may be configurable and variable with respect to a single anatomical plane or with respect to two or more anatomical planes. For example, a subject or a feature of the device may be described as lying within and having adaptability or operability in relation to a single plane. A device may be positioned in a desired location relative to a sagittal plane and may be moveable between a number of adaptable positions or within a range of positions.

For purposes of illustration, the devices and methods of the disclosure are described below with reference to the spine of the human body. However, as will be appreciation by those skilled in the art, the devices and methods can be employed to address any effected bone or joint, including, for example, the hip, the knee, the ankle, the wrist, the elbow, and the shoulder. Additionally, the devices and methods can also be employed with any mammal.

II. Computing Systems

The systems and methods described herein rely on a variety of computer systems, networks and/or digital devices for operation. In order to fully appreciate how the system operates an understanding of suitable computing systems is useful. The systems and methods disclosed herein are enabled as a result of application via a suitable computing system.

Figure 2A:
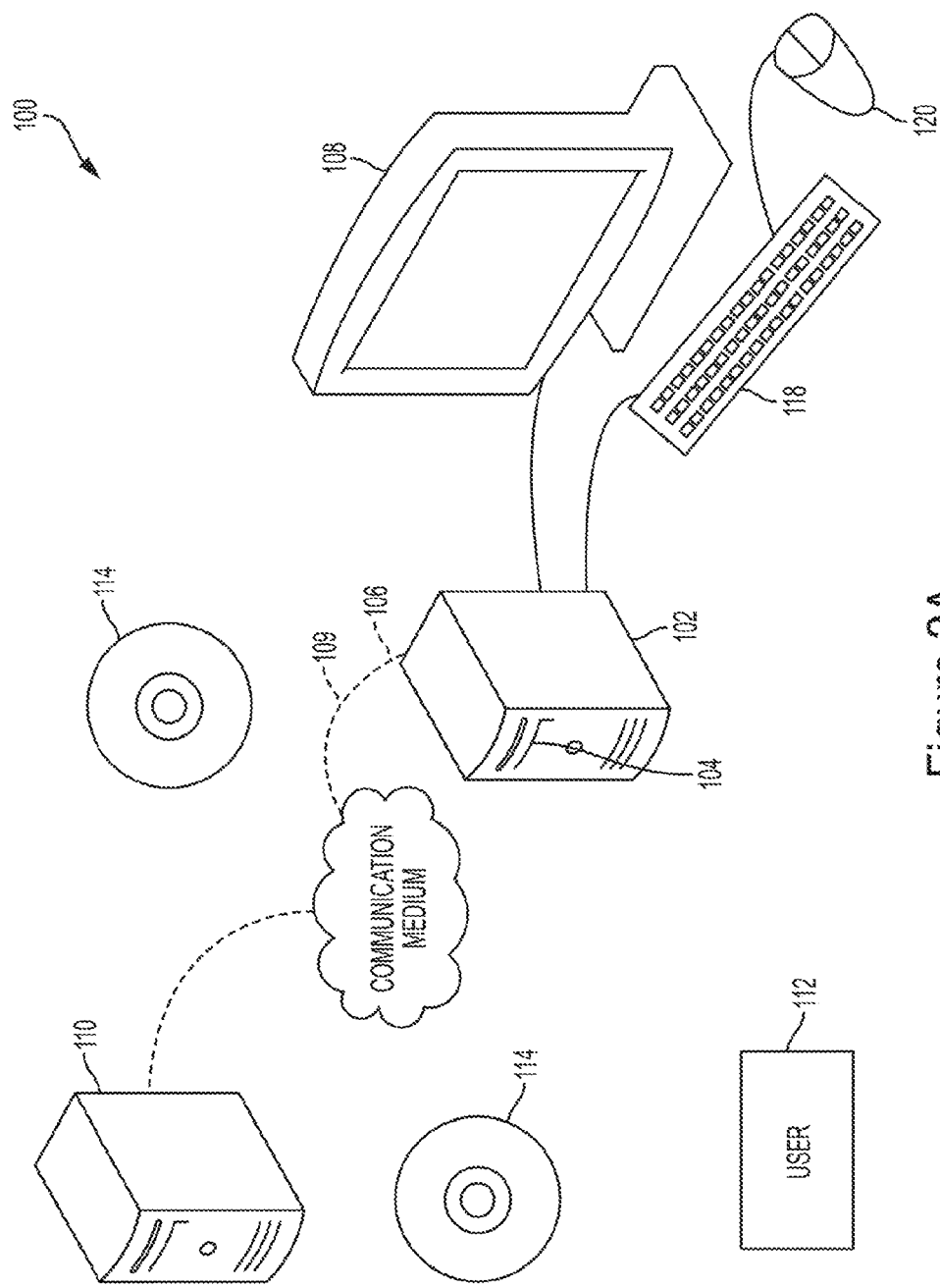
FIG. 2A is a block diagram showing a representative example of a logic device through which clinical data reporting can be achieved.

FIG. 2A is a block diagram showing a representative example logic device through which a browser can be accessed to implement the present disclosure. A computer system (or digital device) 100, which may be understood as a logic apparatus adapted and configured to read instructions from media 114 and/or network port 106, is connectable to a server 110, and has a fixed media 116. The computer system 100 can also be connected to the Internet or an intranet. The system includes central processing unit (CPU) 102, disk drives 104, optional input devices, illustrated as keyboard 118 and/or mouse 120 and optional monitor 108. Data communication can be achieved through, for example, communication medium 109 to a server 110 at a local or a remote location. The communication medium 109 can include any suitable mechanism for transmitting and/or receiving data. For example, the communication medium can be a network connection, a wireless connection or an internet connection. It is envisioned that data relating to the present disclosure can be transmitted over such networks or connections. The computer system can be adapted to communicate with a participant and/or a device used by a participant. The computer system is adaptable to communicate with other computers over the Internet, or with computers via a server.

Figure 2B:
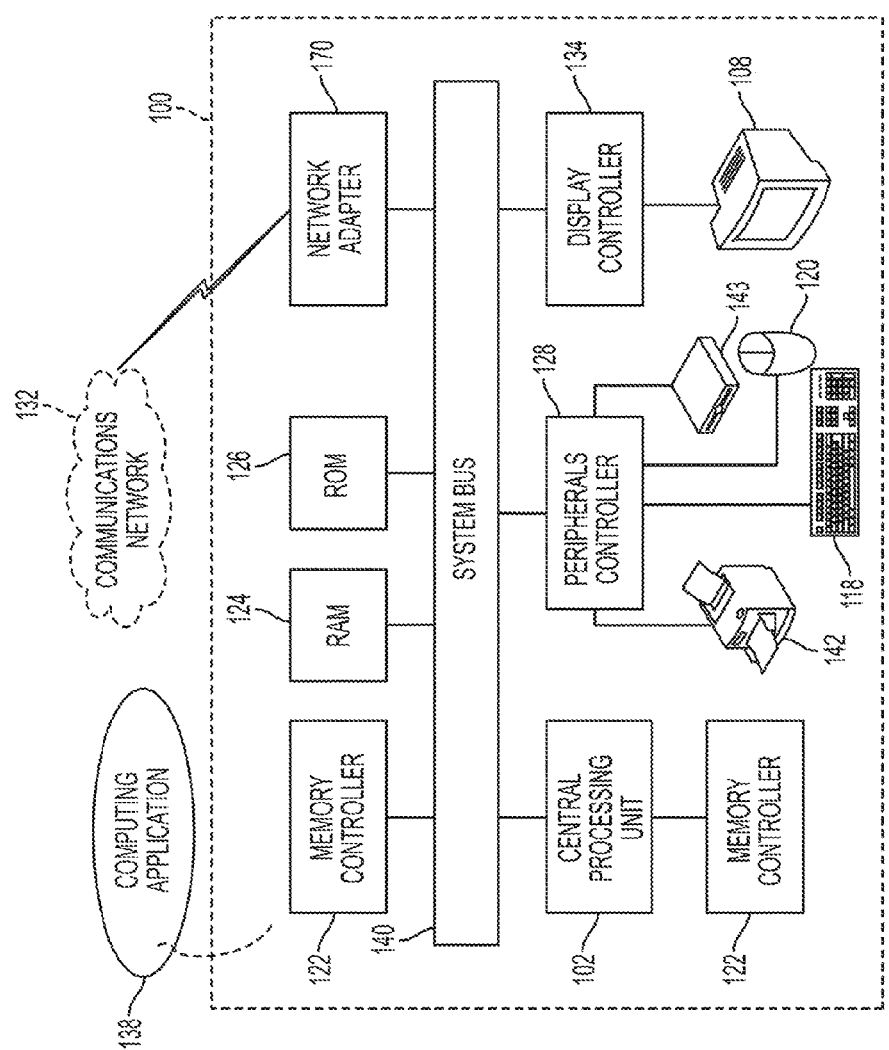
FIG. 2B is a block diagram of an exemplary computing environment through which the clinical data reporting software interface and the surgical navigation and patient positioning can be achieved.

FIG. 2B depicts another exemplary computing system 100. The computing system 100 is capable of executing a variety of computing applications 138, including computing applications, a computing applet, a computing program, or other instructions for operating on computing system 100 to perform at least one function, operation, and/or procedure. Computing system 100 is controllable by computer readable storage media for tangibly storing computer readable instructions, which may be in the form of software. The computer readable storage media adapted to tangibly store computer readable instructions can contain instructions for computing system 100 for storing and accessing the computer readable storage media to read the instructions stored thereon themselves. Such software may be executed within CPU 102 to cause the computing system 100 to perform desired functions. In many known computer servers, workstations and personal computers CPU 102 is implemented by micro-electronic chips CPUs called microprocessors. Optionally, a co-processor, distinct from the main CPU 102, can be provided that performs additional functions or assists the CPU 102. The CPU 102 may be connected to co-processor through an interconnect. One common type of coprocessor is the floating-point coprocessor, also called a numeric or math coprocessor, which is designed to perform numeric calculations faster and better than the general-purpose CPU 102.

As will be appreciated by those skilled in the art, a computer readable medium stores computer data, which data can include computer program code that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor In operation, the CPU 102 fetches, decodes, and executes instructions, and transfers information to and from other resources via the computer's main data-transfer path, system bus 140. Such a system bus connects the components in the computing system 100 and defines the medium for data exchange. Memory devices coupled to the system bus 140 include random access memory (RAM) 124 and read only memory (ROM) 126. Such memories include circuitry that allows information to be stored and retrieved. The ROMs 126 generally contain stored data that cannot be modified. Data stored in the RAM 124 can be read or changed by CPU 102 or other hardware devices. Access to the RAM 124 and/or ROM 126 may be controlled by memory controller 122. The memory controller 122 may provide an address translation function that translates virtual addresses into physical addresses as instructions are executed.

In addition, the computing system 100 can contain peripherals controller 128 responsible for communicating instructions from the CPU 102 to peripherals, such as, printer 142, keyboard 118, mouse 120, and data storage drive 143. Display 108, which is controlled by a display controller 163, is used to display visual output generated by the computing system 100. Such visual output may include text, graphics, animated graphics, and video. The display controller 134 includes electronic components required to generate a video signal that is sent to display 108. Further, the computing system 100 can contain network adaptor 136 which may be used to connect the computing system 100 to an external communications network 132.

III. Networks and Internet Protocol

As is well understood by those skilled in the art, the Internet is a worldwide network of computer networks. Today, the Internet is a public and self-sustaining network that is available to many millions of users. The Internet uses a set of communication protocols called TCP/IP (i.e., Transmission Control Protocol/Internet Protocol) to connect hosts. The Internet has a communications infrastructure known as the Internet backbone. Access to the Internet backbone is largely controlled by Internet Service Providers (ISPs) that resell access to corporations and individuals.

The Internet Protocol (IP) enables data to be sent from one device (e.g., a phone, a Personal Digital Assistant (PDA), a computer, etc.) to another device on a network. There are a variety of versions of IP today, including, e.g., IPv4, IPv6, etc. Other IPs are no doubt available and will continue to become available in the future, any of which can be used without departing from the scope of the disclosure. Each host device on the network has at least one IP address that is its own unique identifier and acts as a connectionless protocol. The connection between end points during a communication is not continuous. When a user sends or receives data or messages, the data or messages are divided into components known as packets. Every packet is treated as an independent unit of data and routed to its final destination—but not necessarily via the same path.

The Open System Interconnection (OSI) model was established to standardize transmission between points over the Internet or other networks. The OSI model separates the communications processes between two points in a network into seven stacked layers, with each layer adding its own set of functions. Each device handles a message so that there is a downward flow through each layer at a sending end point and an upward flow through the layers at a receiving end point. The programming and/or hardware that provides the seven layers of function is typically a combination of device operating systems, application software, TCP/IP and/or other transport and network protocols, and other software and hardware.

Typically, the top four layers are used when a message passes from or to a user and the bottom three layers are used when a message passes through a device (e.g., an IP host device). An IP host is any device on the network that is capable of transmitting and receiving IP packets, such as a server, a router or a workstation. Messages destined for some other host are not passed up to the upper layers but are forwarded to the other host. The layers of the OSI model are listed below. Layer 7 (i.e., the application layer) is a layer at which, e.g., communication partners are identified, quality of service is identified, user authentication and privacy are considered, constraints on data syntax are identified, etc. Layer 6 (i.e., the presentation layer) is a layer that, e.g., converts incoming and outgoing data from one presentation format to another, etc. Layer 5 (i.e., the session layer) is a layer that, e.g., sets up, coordinates, and terminates conversations, exchanges and dialogs between the applications, etc. Layer-4 (i.e., the transport layer) is a layer that, e.g., manages end-to-end control and error-checking, etc. Layer-3 (i.e., the network layer) is a layer that, e.g., handles routing and forwarding, etc. Layer-2 (i.e., the data-link layer) is a layer that, e.g., provides synchronization for the physical level, does bit-stuffing and furnishes transmission protocol knowledge and management, etc. The Institute of Electrical and Electronics Engineers (IEEE) sub-divides the data-link layer into two further sub-layers, the MAC (Media Access Control) layer that controls the data transfer to and from the physical layer and the LLC (Logical Link Control) layer that interfaces with the network layer and interprets commands and performs error recovery. Layer 1 (i.e., the physical layer) is a layer that, e.g., conveys the bit stream through the network at the physical level. The IEEE sub-divides the physical layer into the PLCP (Physical Layer Convergence Procedure) sub-layer and the PMD (Physical Medium Dependent) sub-layer.

IV. Wireless Networks

Wireless networks can incorporate a variety of types of mobile devices, such as, e.g., cellular and wireless telephones, PCs (personal computers), laptop computers, wearable computers, cordless phones, pagers, headsets, printers, PDAs, etc. For example, mobile devices may include digital systems to secure fast wireless transmissions of voice and/or data. Typical mobile devices include some or all of the following components: a transceiver (for example a transmitter and a receiver, including a single chip transceiver with an integrated transmitter, receiver and, if desired, other functions); an antenna; a processor; display; one or more audio transducers (for example, a speaker or a microphone as in devices for audio communications); electromagnetic data storage (such as ROM, RAM, digital data storage, etc., such as in devices where data processing is provided); memory; flash memory; and/or a full chip set or integrated circuit; interfaces (such as universal serial bus (USB), coder-decoder (CODEC), universal asynchronous receiver-transmitter (UART), phase-change memory (PCM), etc.). Other components can be provided without departing from the scope of the disclosure.

Wireless LANs (WLANs) in which a mobile user can connect to a local area network (LAN) through a wireless connection may be employed for wireless communications. Wireless communications can include communications that propagate via electromagnetic waves, such as light, infrared, radio, and microwave. There are a variety of WLAN standards that currently exist, such as Bluetooth®, IEEE 802.11, and the obsolete HomeRF.

By way of example, Bluetooth products may be used to provide links between mobile computers, mobile phones, portable handheld devices, personal digital assistants (PDAs), and other mobile devices and connectivity to the Internet. Bluetooth is a computing and telecommunications industry specification that details how mobile devices can easily interconnect with each other and with non-mobile devices using a short-range wireless connection. Bluetooth creates a digital wireless protocol to address end-user problems arising from the proliferation of various mobile devices that need to keep data synchronized and consistent from one device to another, thereby allowing equipment from different vendors to work seamlessly together.

An IEEE standard, IEEE 802.11, specifies technologies for wireless LANs and devices. Using 802.11, wireless networking may be accomplished with each single base station supporting several devices. In some examples, devices may come pre-equipped with wireless hardware or a user may install a separate piece of hardware, such as a card, that may include an antenna. By way of example, devices used in 802.11 typically include three notable elements, whether or not the device is an access point (AP), a mobile station (STA), a bridge, a personal computing memory card International Association (PCMCIA) card (or PC card) or another device: a radio transceiver; an antenna; and a MAC (Media Access Control) layer that controls packet flow between points in a network.

In addition, Multiple Interface Devices (MIDs) may be utilized in some wireless networks. MIDs may contain two independent network interfaces, such as a Bluetooth interface and an 802.11 interface, thus allowing the MID to participate on two separate networks as well as to interface with Bluetooth devices. The MID may have an IP address and a common IP (network) name associated with the IP address.

Wireless network devices may include, but are not limited to Bluetooth devices, WiMAX (Worldwide Interoperability for Microwave Access), Multiple Interface Devices (MIDs), 802.11x devices (IEEE 802.11 devices including, 802.11a, 802.11b and 802.11g devices), HomeRF (Home Radio Frequency) devices, Wi-Fi (Wireless Fidelity) devices, GPRS (General Packet Radio Service) devices, 3 G cellular devices, 2.5 G cellular devices, GSM (Global System for Mobile Communications) devices, EDGE (Enhanced Data for GSM Evolution) devices, TDMA type (Time Division Multiple Access) devices, or CDMA type (Code Division Multiple Access) devices, including CDMA2000. Each network device may contain addresses of varying types including but not limited to an IP address, a Bluetooth Device Address, a Bluetooth Common Name, a Bluetooth IP address, a Bluetooth IP Common Name, an 802.11 IP Address, an 802.11 IP common Name, or an IEEE MAC address.

Wireless networks can also involve methods and protocols found in, Mobile IP (Internet Protocol) systems, in PCS systems, and in other mobile network systems. With respect to Mobile IP, this involves a standard communications protocol created by the Internet Engineering Task Force (IETF). With Mobile IP, mobile device users can move across networks while maintaining their IP Address assigned once. See Request for Comments (RFC) 3344. NB: RFCs are formal documents of the Internet Engineering Task Force (IETF). Mobile IP enhances Internet Protocol (IP) and adds a mechanism to forward Internet traffic to mobile devices when connecting outside their home network. Mobile IP assigns each mobile node a home address on its home network and a care-of-address (CoA) that identifies the current location of the device within a network and its subnets. When a device is moved to a different network, it receives a new care-of address. A mobility agent on the home network can associate each home address with its care-of address. The mobile node can send the home agent a binding update each time it changes its care-of address using Internet Control Message Protocol (ICMP).

In basic IP routing (e.g., outside mobile IP), routing mechanisms rely on the assumptions that each network node has a constant attachment point to the Internet and that each node's IP address identifies the network link it is attached to. In this document, the terminology "node" includes a connection point, which can include a redistribution point or an end point for data transmissions, and which can recognize, process and/or forward communications to other nodes. For example, Internet routers can look at an IP address prefix or the like identifying a device's network. Then, at a network level, routers can look at a set of bits identifying a particular subnet. Then, at a subnet level, routers can look at a set of bits identifying a particular device. With typical mobile IP communications, if a user disconnects a mobile device from the Internet and tries to reconnect it at a new subnet, then the device has to be reconfigured with a new IP address, a proper netmask and a default router. Otherwise, routing protocols would not be able to deliver the packets properly.

Figure 2C:
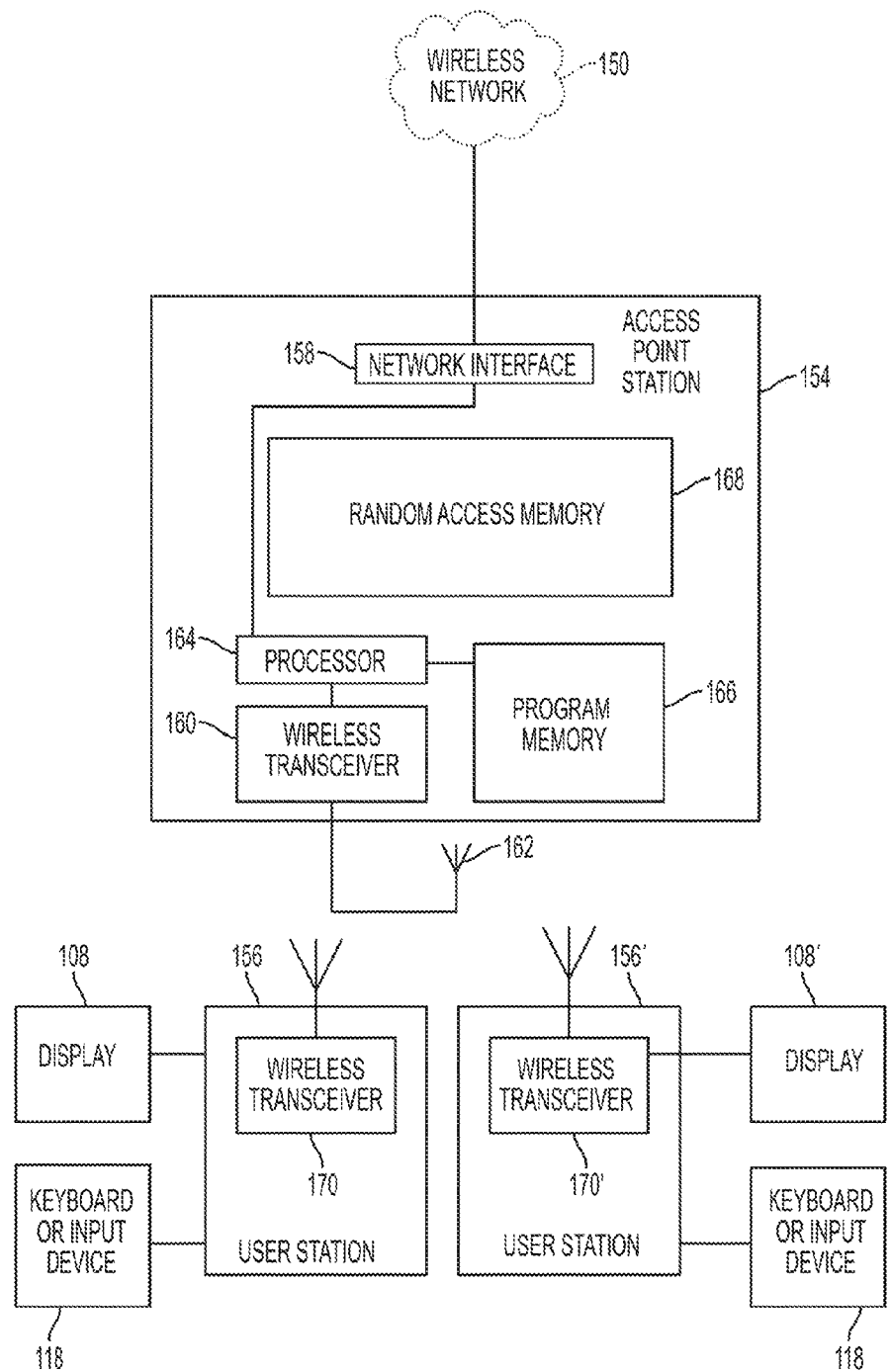
FIG. 2C is an illustrative architectural diagram showing some structure that can be employed by devices through which the clinical data reporting software interface and the surgical navigation and patient positioning can be achieved.

FIG. 2C depicts components that can be employed in system configurations enabling the systems and technical effect of this disclosure, including wireless access points to which client devices communicate. In this regard, FIG. 2C shows a wireless network 150 connected to a wireless local area network (WLAN) 152. The WLAN 152 includes an access point (AP) 154 and a number of user stations 156, 156'. For example, the network 150 can include the Internet or a corporate data processing network. The access point 154 can be a wireless router, and the user stations 156, 156' can be portable computers, personal desk-top computers, PDAs, portable voice-over-IP telephones and/or other devices. The access point 154 has a network interface 158 linked to the network 150, and a wireless transceiver in communication with the user stations 156, 156'. For example, the wireless transceiver 160 can include an antenna 162 for radio or microwave frequency communication with the user stations 156, 156'. The access point 154 also has a processor 164, a program memory 166, and a random access memory 168. The user station 156 has a wireless transceiver 170 including an antenna 172 for communication with the access point station 154. In a similar fashion, the user station 156' has a wireless transceiver 170' and an antenna 172 for communication to the access point 154. By way of example, in some embodiments an authenticator could be employed within such an access point (AP) and/or a supplicant or peer could be employed within a mobile node or user station. Desktop 108 and key board 118 or input devices can also be provided with the user status.

V. Media Independent Handover Services

In IEEE P802.21/D.01.09, September 2006, entitled Draft IEEE Standard for Local and Metropolitan Area Networks: Media Independent Handover Services, among other things, the document specifies 802 media access-independent mechanisms that optimize handovers between 802 systems and cellular systems. The IEEE 802.21 standard defines extensible media access independent mechanisms that enable the optimization of handovers between heterogeneous 802 systems and may facilitate handovers between 802 systems and cellular systems. "The scope of the IEEE 802.21 (Media Independent Handover) standard is to develop a specification that provides link layer intelligence and other related network information to upper layers to optimize handovers between heterogeneous media. This includes links specified by 3GPP, 3GPP2 and both wired and wireless media in the IEEE 802 family of standards. Note, in this document, unless otherwise noted, "media" refers to method/mode of accessing a telecommunication system (e.g. cable, radio, satellite, etc.), as opposed to sensory aspects of communication (e.g. audio, video, etc.)." See 1.1 of I.E.E.E. P802.21/D.01.09, September 2006, entitled Draft IEEE Standard for Local and Metropolitan Area Networks: Media Independent Handover Services, the entire contents of which document is incorporated herein into and as part of this patent application. Other IEEE, or other such standards on protocols can be relied on as appropriate or desirable.

Figure 3:
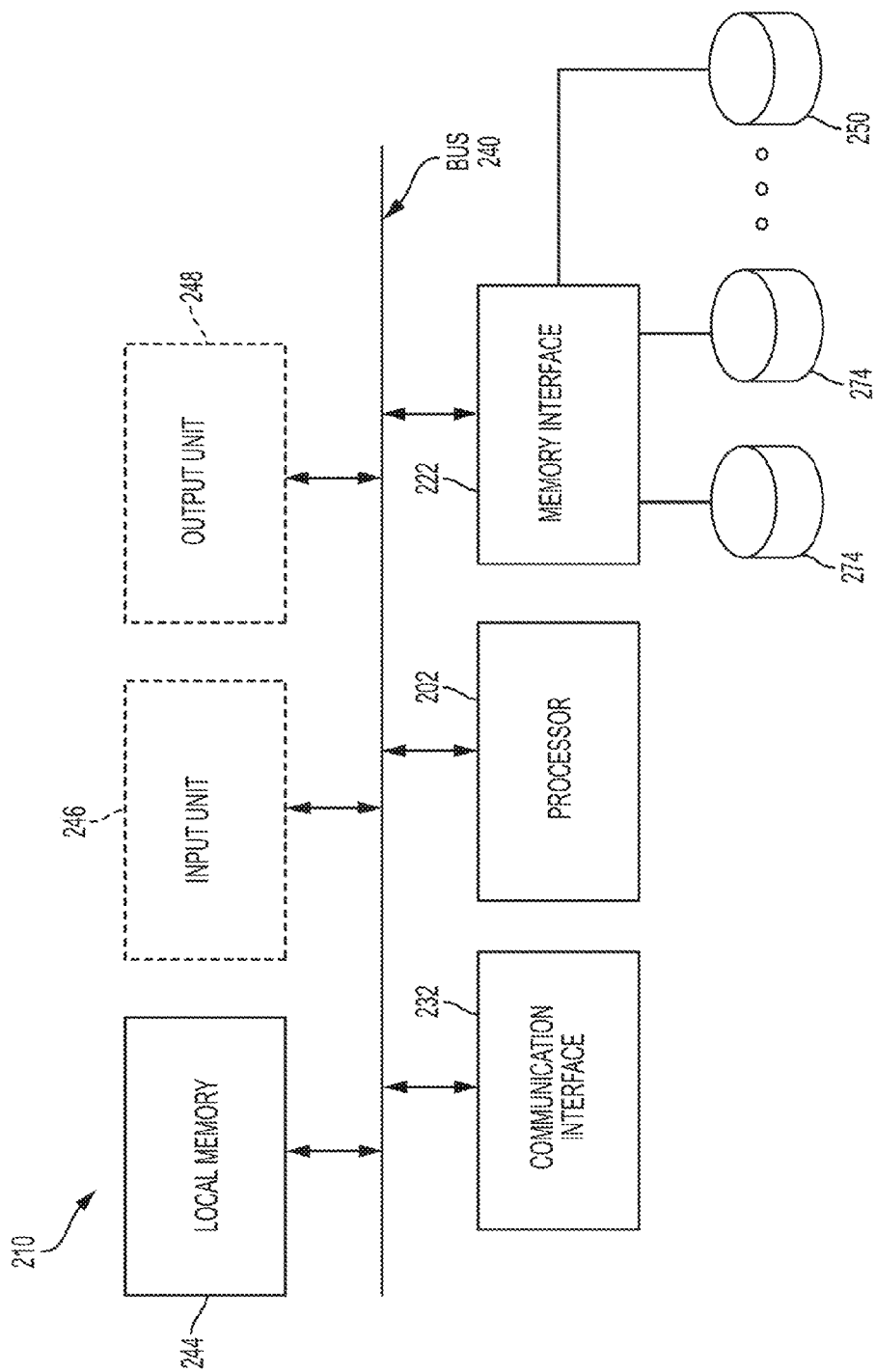
FIG. 3 is an exemplary diagram of a server in an implementation suitable for use in a system where the clinical data reporting software interface and the surgical navigation and patient positioning can be achieved.

FIG. 3 is an exemplary diagram of a server 210 in an implementation consistent with the principles of the disclosure to achieve the desired technical effect and transformation. Server 210 may include a bus 240, a processor 202, a local memory 244, one or more optional input units 246, one or more optional output units 248, a communication interface 232, and a memory interface 222. Bus 240 may include one or more conductors that permit communication among the components of chunk server 250.

Processor 202 may include any type of conventional processor or microprocessor that interprets and executes instructions. Local memory 244 may include a random access memory (RAM) or another type of dynamic storage device that stores information and instructions for execution by processor 202 and/or a read only memory (ROM) or another type of static storage device that stores static information and instructions for use by processor 202.

Input unit 246 may include one or more conventional mechanisms that permit an operator to input information to a server 110, such as a keyboard 118, a mouse 120 (shown in FIG. 2), a pen, voice recognition and/or biometric mechanisms, etc. Output unit 248 may include one or more conventional mechanisms that output information to the operator, such as a display 134, a printer 130 (shown in FIG. 2), a speaker, etc. Communication interface 232 may include any transceiver-like mechanism that enables chunk server 250 to communicate with other devices and/or systems. For example, communication interface 232 may include mechanisms for communicating with master and clients.

Memory interface 222 may include a memory controller 122. Memory interface 222 may connect to one or more memory devices, such as one or more local disks 274, and control the reading and writing of chunk data to/from local disks 276. Memory interface 222 may access chunk data using a chunk handle and a byte range within that chunk.

Figure 4:
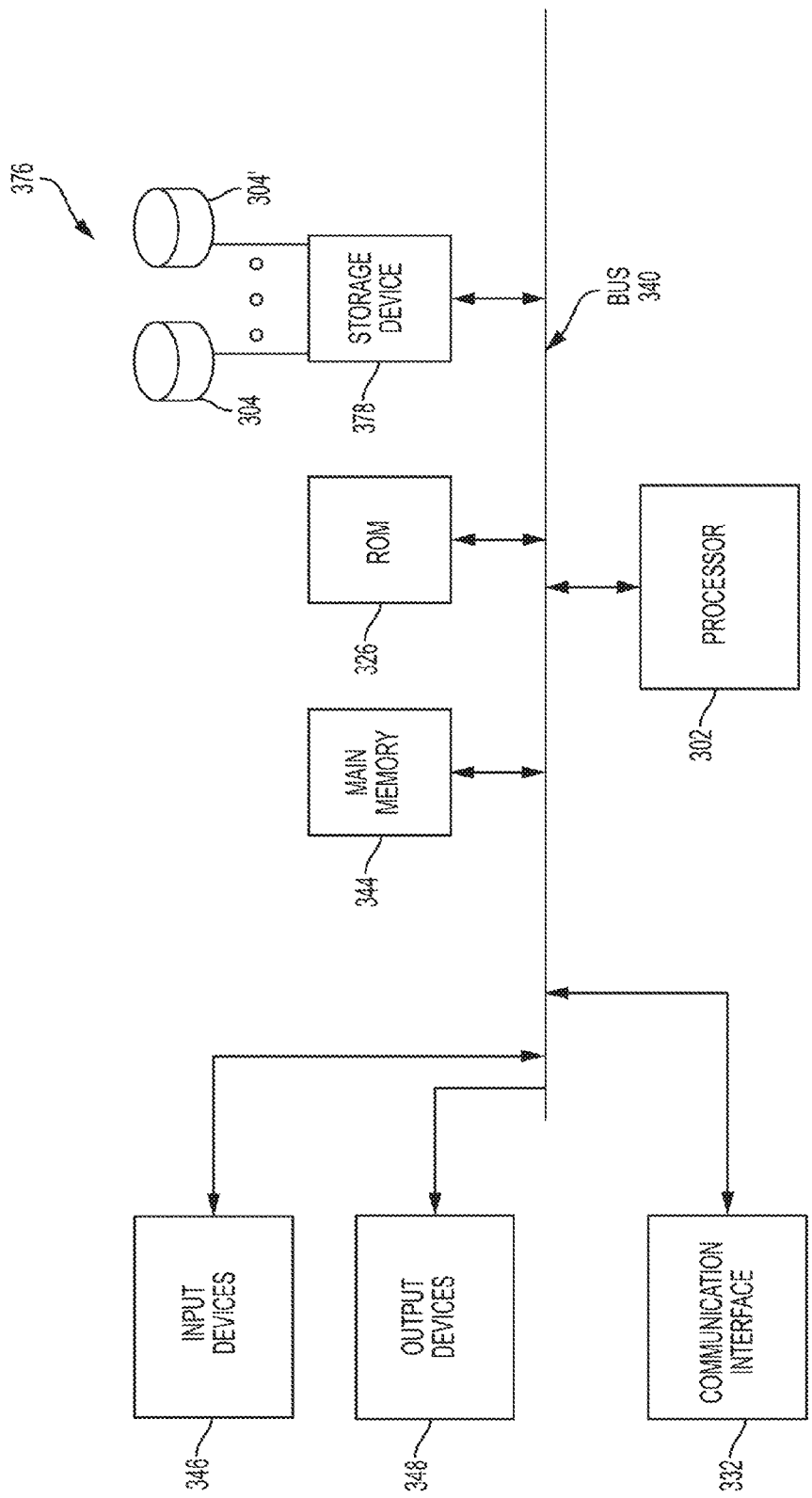
FIG. 4 is an exemplary diagram of a master system in an implementation suitable for use in a system where the clinical data reporting software interface and the surgical navigation and patient positioning can be achieved.

FIG. 4 is an exemplary diagram of a master system 376 suitable for use in an implementation consistent with the principles of the disclosure to achieve the desired technical effect and transformation. Master system 376 may include a bus 340, a processor 302, a main memory 344, a ROM 326, a storage device 378, one or more input devices 346, one or more output devices 348, and a communication interface 332. Bus 340 may include one or more conductors that permit communication among the components of master system 374.

Processor 302 may include any type of conventional processor or microprocessor that interprets and executes instructions. Main memory 344 may include a RAM or another type of dynamic storage device that stores information and instructions for execution by processor 302. ROM 326 may include a conventional ROM device or another type of static storage device that stores static information and instructions for use by processor 302. Storage device 378 may include a magnetic and/or optical recording medium and its corresponding drive. For example, storage device 378 may include one or more local disks that provide persistent storage.

Input devices 346 used to achieve the desired technical effect and transformation may include one or more conventional mechanisms that permit an operator to input information to the master system 374, such as a keyboard 118, a mouse 120, (shown in FIG. 2) a pen, voice recognition and/or biometric mechanisms, etc. Output devices 348 may include one or more conventional mechanisms that output information to the operator, including a display 108, a printer 142 (shown in FIG. 1), a speaker, etc. Communication interface 332 may include any transceiver-like mechanism that enables master system 374 to communicate with other devices and/or systems. For example, communication interface 332 may include mechanisms for communicating with servers and clients as shown above.

Master system 376 used to achieve the desired technical effect and transformation may maintain file system metadata within one or more computer readable mediums, such as main memory 344 and/or storage device.

The computer implemented system provides a storage and delivery base which allows users to exchange services and information openly on the Internet used to achieve the desired technical effect and transformation. A user will be enabled to operate as both a consumer and producer of any and all digital content or information through one or more master system servers.

A user executes a browser to view digital content items and can connect to the front end server via a network, which is typically the Internet, but can also be any network, including but not limited to any combination of a LAN, a MAN, a WAN, a mobile, wired or wireless network, a private network, or a virtual private network. As will be understood, a very large numbers (e.g., millions) of users are supported and can be in communication with the website at any time. The user may include a variety of different computing devices. Examples of user devices include, but are not limited to, personal computers, digital assistants, personal digital assistants, cellular phones, mobile phones, smart phones or laptop computers.

The browser can include any application that allows users to access web pages on the World Wide Web. Suitable applications include, but are not limited to, Microsoft Internet Explorer®, Netscape Navigator®, Mozilla® Firefox, Apple® Safari or any application adapted to allow access to web pages on the World Wide Web. The browser can also include a video player (e.g., Flash™ from Adobe Systems, Inc.), or any other player adapted for the video file formats used in the video hosting website. Alternatively, videos can be accessed by a standalone program separate from the browser. A user can access a video from the website by, for example, browsing a catalog of digital content, conducting searches on keywords, reviewing aggregate lists from other users or the system administrator (e.g., collections of videos forming channels), or viewing digital content associated with particular user groups (e.g., communities).

VI. Computer Network Environment

Figure 5:
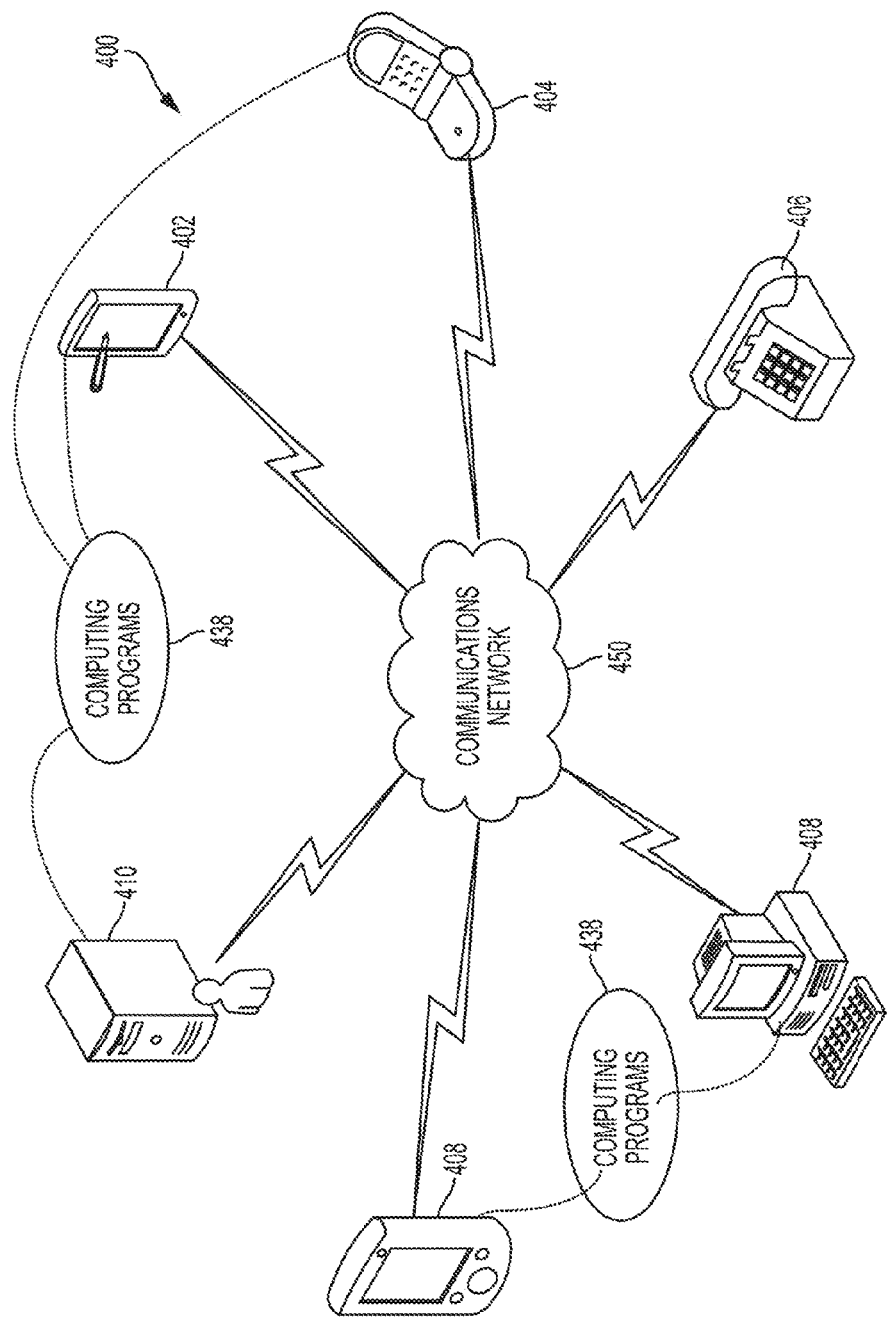
FIG. 5 is a block diagram showing the cooperation of exemplary components of a system suitable for use in a system where the clinical data reporting software interface and the surgical navigation and patient positioning can be achieved.

Computing system 100, described above, can be deployed as part of a computer network used to achieve the desired technical effect and transformation. In general, the above description for computing environments applies to both server computers and client computers deployed in a network environment. FIG. 5 illustrates an exemplary illustrative networked computing environment 400, with a server in communication with client computers via a communications network 450. As shown in FIG. 5, server 410 may be interconnected via a communications network 450 (which may be either of, or a combination of a fixed-wire or wireless LAN, WAN, intranet, extranet, peer-to-peer network, virtual private network, the Internet, or other communications network) with a number of client computing environments such as tablet personal computer 402, mobile telephone 404, telephone 406, personal computer 402, and personal digital assistant 408. In a network environment in which the communications network 450 is the Internet, for example, server 410 can be dedicated computing environment servers operable to process and communicate data to and from client computing environments via any of a number of known protocols, such as, hypertext transfer protocol (HTTP), file transfer protocol (FTP), simple object access protocol (SOAP), or wireless application protocol (WAP). Other wireless protocols can be used without departing from the scope of the disclosure, including, for example Wireless Markup Language (WML), DoCoMo i-mode (used, for example, in Japan) and XHTML Basic. Additionally, networked computing environment 400 can utilize various data security protocols such as secured socket layer (SSL) or pretty good privacy (PGP). Each client computing environment can be equipped with operating system 438 operable to support one or more computing applications, such as a web browser (not shown), or other graphical user interface (not shown), or a mobile desktop environment (not shown) to gain access to server computing environment 400.

In operation, a user (not shown) may interact with a computing application running on a client computing environment to obtain desired data and/or computing applications. The data and/or computing applications may be stored on server computing environment 400 and communicated to cooperating users through client computing environments over exemplary communications network 450. The computing applications, described in more detail below, are used to achieve the desired technical effect and transformation set forth. A participating user may request access to specific data and applications housed in whole or in part on server computing environment 400. These data may be communicated between client computing environments and server computing environments for processing and storage. Server computing environment 400 may host computing applications, processes and applets for the generation, authentication, encryption, and communication data and applications and may cooperate with other server computing environments (not shown), third party service providers (not shown), network attached storage (NAS) and storage area networks (SAN) to realize application/data transactions.

VII. Media Independent Information Service

The Media Independent Information Service (MIIS) provides a framework and corresponding mechanisms by which an MIHF entity may discover and obtain network information existing within a geographical area to facilitate handovers. Additionally or alternatively, neighboring network information discovered and obtained by this framework and mechanisms can also be used in conjunction with user and network operator policies for optimum initial network selection and access (attachment), or network re-selection in idle mode.

MIIS primarily provides a set of information elements (IEs), the information structure and its representation, and a query/response type of mechanism for information transfer. The information can be present in some information server from which, e.g., an MIHF in the Mobile Node (MN) can access it.

Depending on the type of mobility, support for different types of information elements may be necessary for performing handovers. MIIS provides the capability for obtaining information about lower layers such as neighbor maps and other link layer parameters, as well as information about available higher layer services such as Internet connectivity.

MIIS provides a generic mechanism to allow a service provider and a mobile user to exchange information on different handover candidate access networks. The handover candidate information can include different access technologies such as IEEE 802 networks, 3GPP networks and 3GPP2 networks. The MIIS also allows this collective information to be accessed from any single network. For example, by using an IEEE 802.11 access network, it can be possible to get information not only about all other IEEE 802 based networks in a particular region but also about 3GPP and 3GPP2 networks. Similarly, using, e.g., a 3GPP2 interface, it can be possible to get access to information about all IEEE 802 and 3GPP networks in a given region. This capability allows the MN to use its currently active access network and inquire about other available access networks in a geographical region. Thus, a MN is freed from the burden of powering up each of its individual radios and establishing network connectivity for the purpose of retrieving heterogeneous network information. MIIS enables this functionality across all available access networks by providing a uniform way to retrieve heterogeneous network information in any geographical area.

VIII. Software Programs Implementable in the Computing and Network Environments to Achieve a Desired Technical Effect or Transformation A. Clinical Data Reporting Software Interface A clinical data reporting software interface comprises a communications network, communication medium, input and output devices, computing application and software application that communicate and compute data through a process of initialization by user, interpretation of results, and comparison with aggregated data.

The clinical data reporting software interface integrates user preferences for procedures of interest along with associated risk factors and risk mitigation factors to facilitate interpretation of patient specific results for specific kinematic dysfunctions, at each spine level. A user profile is also created during the initialization step and generally does not change from patient-to-patient for a particular user, however this profile is changeable by the user.

Figure 6:
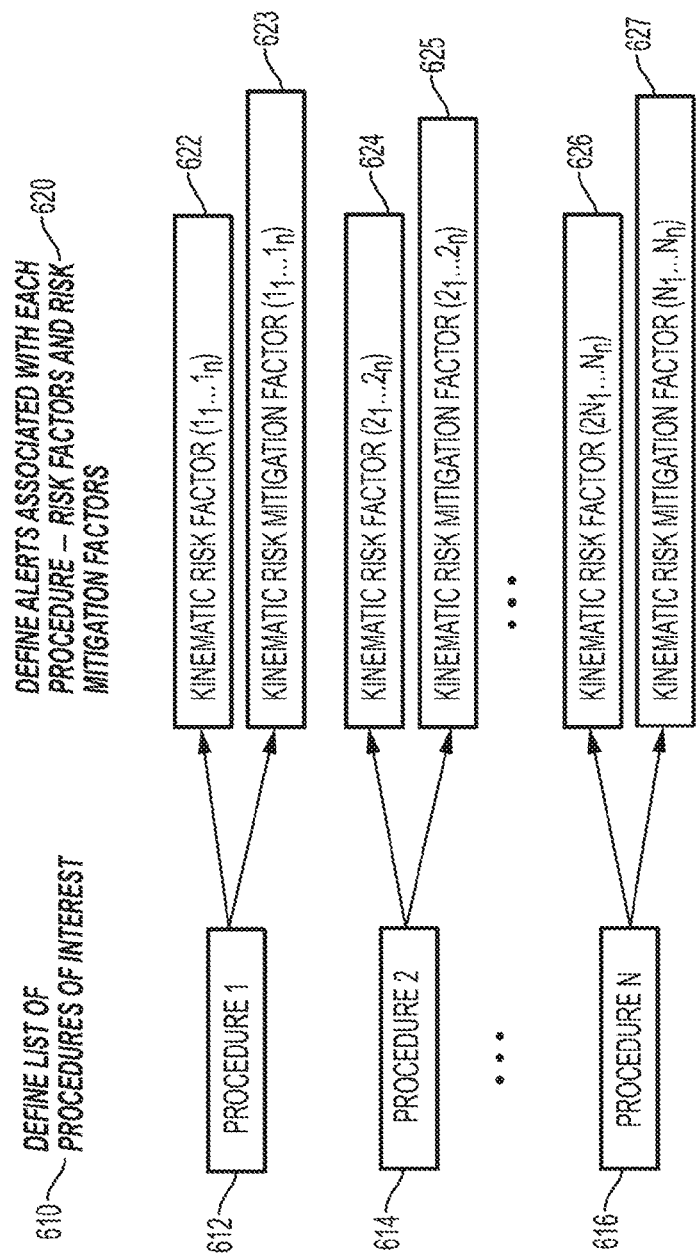
FIG. 6 is a simplified block diagram of an initialization step for the clinical data reporting software interface. This initialization step is performed once by a user prior to a first use, and can be updated as needed. In this step the user defines a list of procedures of interest and associated alerts based on risk factors and risk mitigation factors.

FIG. 6 is a simplified block diagram of an initialization process for the clinical data reporting software interface which is performed once by the user, and can be updated as needed. In this step the user defines a list of one or more procedures of interest 610, e.g., Procedure 1 612, Procedure 2 614 through Procedure N 616. These procedures can represent a range of potential surgeries that a given user commonly prescribes to his or her patients. Once the list of procedures of interest for a given user is defined, then associated alerts 620 are also defined for each procedures based on one or more kinematic risk factors and one or more kinematic risk mitigation factors associated with each procedure. For example, the user would define one or more kinematic risk factors 622, 624, 626 corresponding to each of the procedures 612, 614, 616 as well as one or more kinematic risk mitigation factors 623, 625, 627 corresponding to each of the procedures. In some aspects, a particular procedure may have no mitigation factors and no risk factors, one or more mitigation factors and no risk factors, no mitigation factors and one or more risk factors, or one or more mitigation factors and one or more risk factors. For purposes of illustration, FIG. 7e provides examples of kinematic risk factors and kinematic risk mitigation factors for some commonly prescribed spine surgeries.

The process of analyzing and interpreting results within the clinical data reporting software interface is performed each time a subject (patient) undergoes kinematic testing. The results for each subject tested indicates one or more specific kinematic dysfunctions that have been detected. In the context of the spine, the one or more dysfunctions can be provided at each spine level. The combination of risk and risk mitigation factors are defined as specific alerts in the reporting system that can be presented to the user (surgeon) for evaluation of changes to a planned procedure for a particular patient.

Figure 7A:
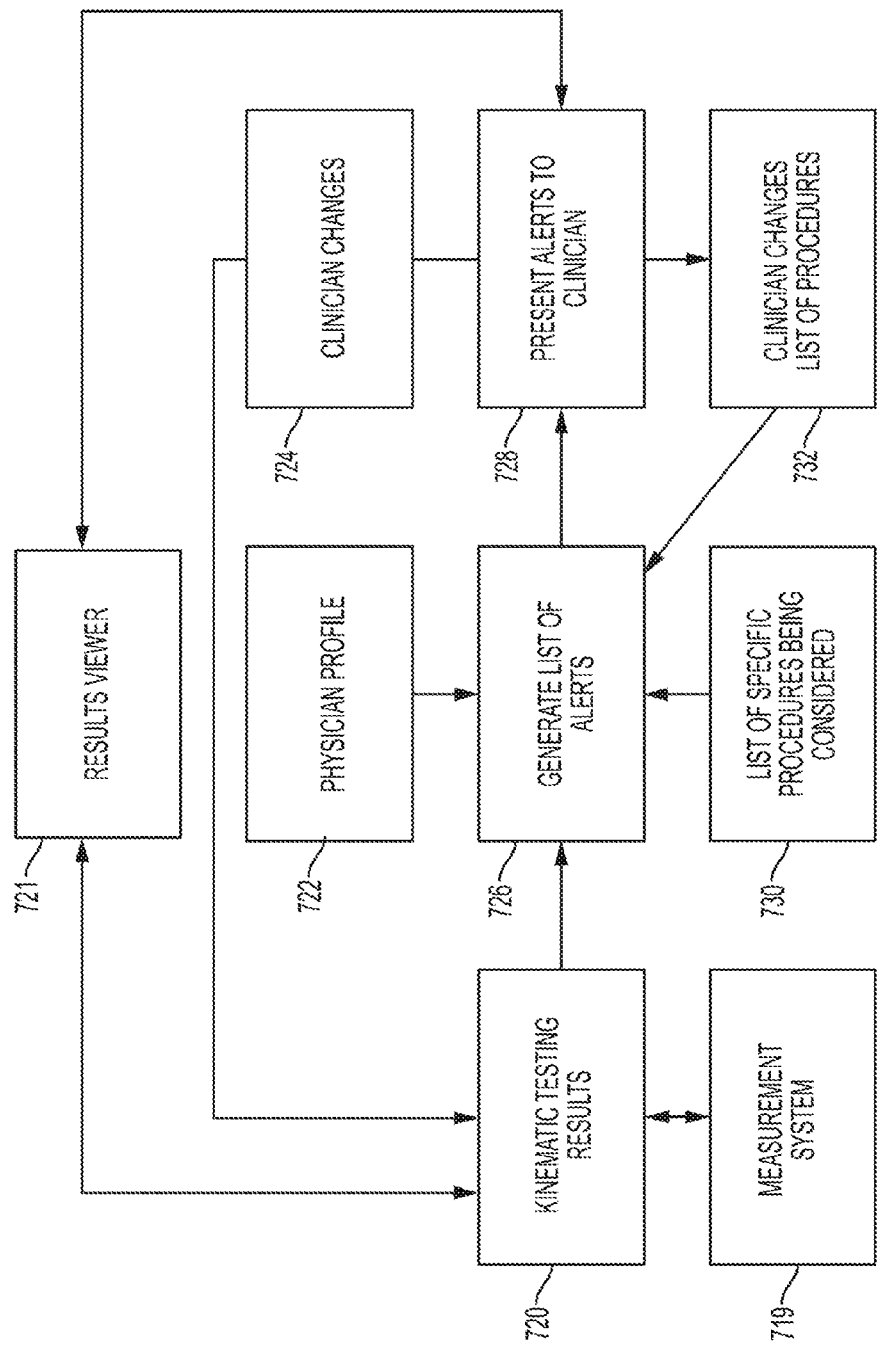
FIG. 7a is a simplified block diagram of a step for interpreting response the clinical data reporting software interface. This step is performed when a subject undergoes kinematic testing. Results which indicate specific kinematic dysfunctions detected at, for example, each spine level are interpreted based on threshold limits which are set and changed interactively by the user.

FIG. 7a is a block diagram illustrating the process of interpreting results within the clinical data reporting software interface. For example, the measurement system 719 communicates kinematic testing results for each patient 720. The kinematic testing results can be, for example, an identification of specific kinematic dysfunctions that have been detected at each spine level. Based on the kinetic testing results 720 a list of alerts for each procedure being considered is generated 726 which takes into consideration the user (physician) profile created during the initialization process 722 and a list of specific procedures being considered for the particular patient 730. The alerts are presented to the clinician 728 at which point the clinician can change the threshold limits for detecting kinematic dysfunctions for that patient 724, or change a list of procedures being considered 732. Results of this process are presented to the user via the results viewer 721.

FIGS. 7b and 7c show a first and second page of a two-page sample form that represents one embodiment of data a user (e.g., surgeon) would provide during the initialization process, the data from which would be part of the user profile described above with respect to FIG. 6.

Figure 7D:
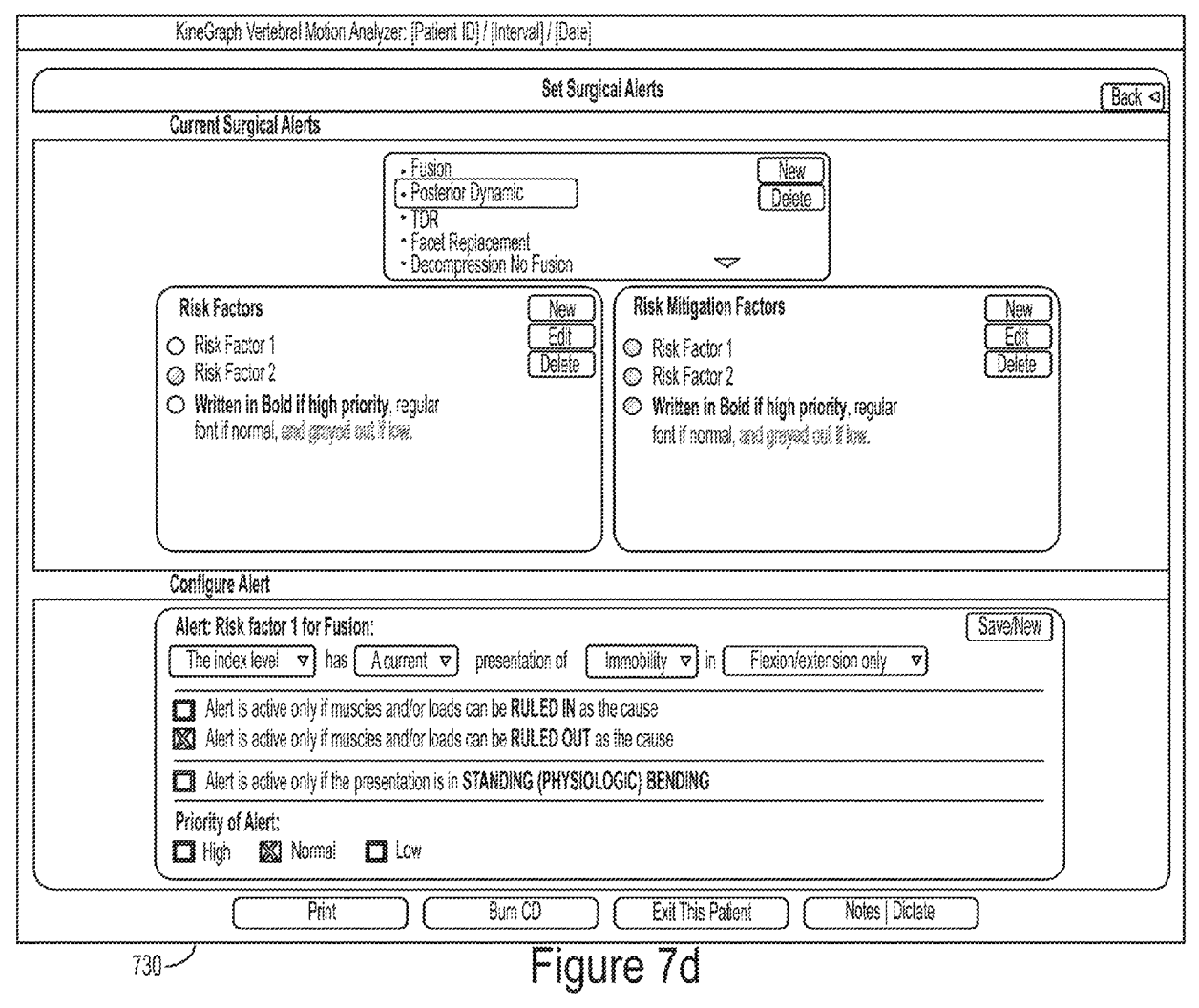

FIG. 7d is a screen shot 730 which illustrates how the alerts that are configured during the initialization process can be changed by the user using the clinical data reporting interface. In this figure, the user can construct alerts using drop down menus and check boxes, view existing alerts, assign priority to alerts, edit alerts, delete alerts, and specify the exact configuration of the alerts with respect to which bending mode the alert is based on. Any changes made would then be saved in the user profile.

FIG. 7e shows the types of alerts that, according to one embodiment, a spine surgeon may want to be warned about, both in terms of "Good" and "Bad" risk mitigation factors alerts based on the user profile set-up during the initiation process.

Figure 7F:
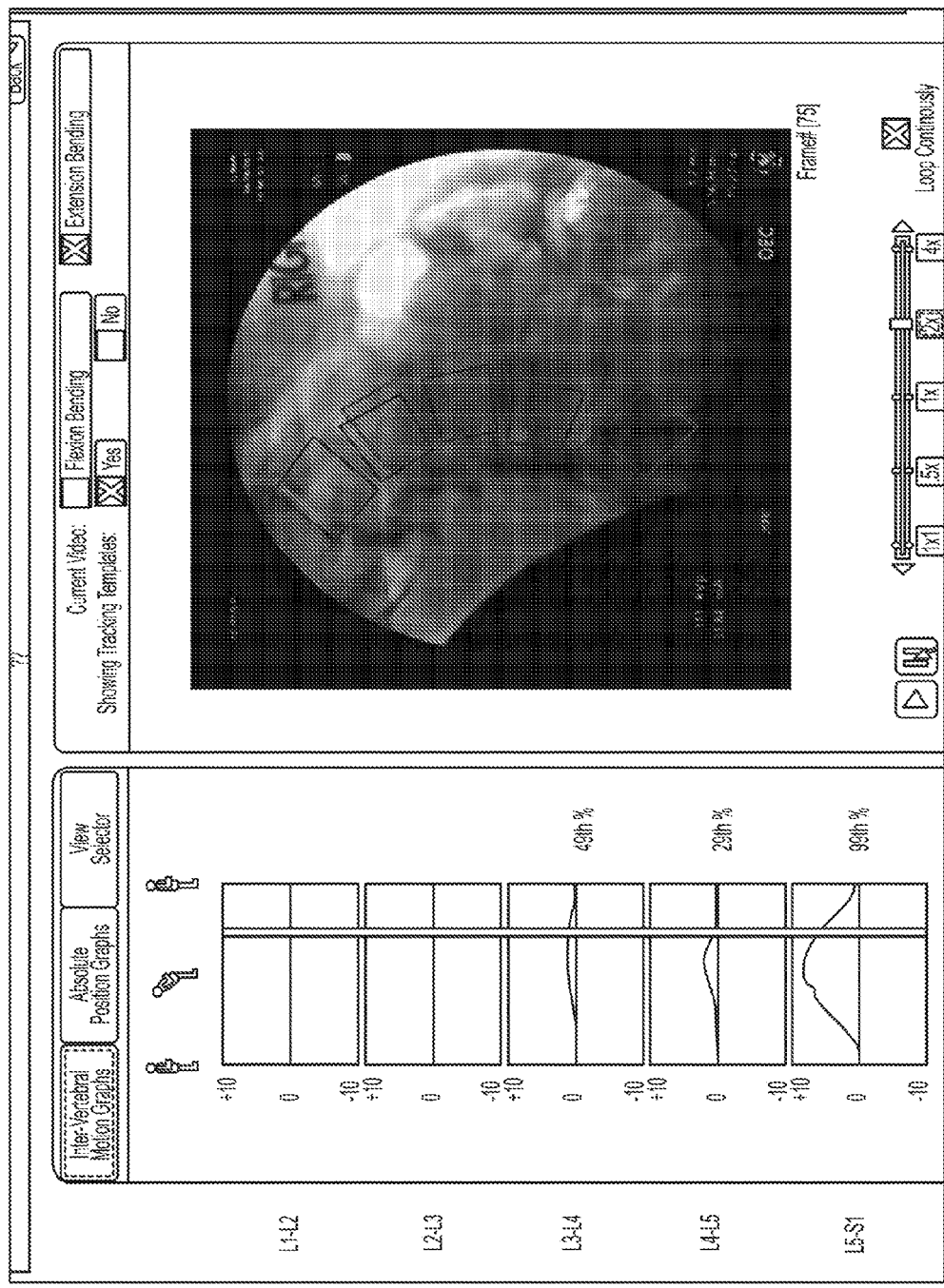
FIG. 7f illustrates a screen shot for viewing results including moving video images along with templates, graph, and numeric data; that can be part of the results viewing capability of the clinical data reporting software interface.

Additionally, users can view kinematic testing results via the results viewer. Moreover, the results viewer allows for multiple types of results viewing, including the viewing of moving video images along with templates, graph, and numeric data, as depicted in the screen shot 740 presented as FIG. 7f. As illustrated in FIG. 7f, moving medical images can be played as an image sequence, and displayed alongside graph data depicting the relative motion between anatomical landmarks across a set of moving images, wherein a cursor (a vertical line in this case) moves across the graphs showing the point on each graph that corresponds to the specific image frame being presented. Template data, showing the measured position of each tracked landmark on the moving image sequences, is also displayed by being overlaid on top of each individual frame of the moving image sequences, such that the user can confirm that the templates are placed appropriately on the anatomical landmarks about which relative motion data is being presented. Additional quantitative data is presented alongside the graphs and image sequences. Different data from different bending modes can be accessed via this capability, and the user is provided with tools to let them determine which data to view.

Figure 7G:
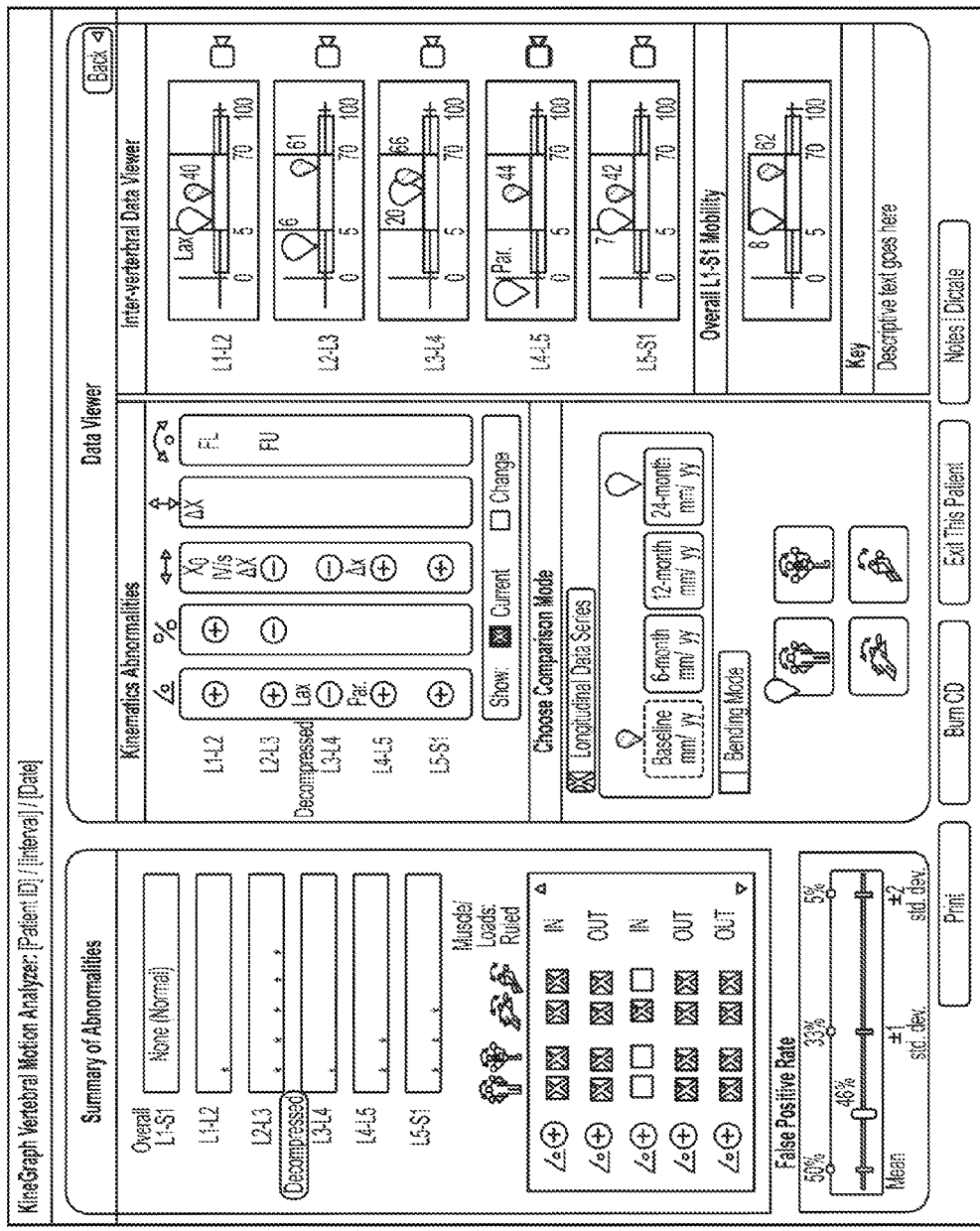
FIG. 7g is a screen shot illustrating the results viewing capability of the clinical data reporting software interface, which facilitates a user's interaction with quantitative data regarding the detection of specific kinematic dysfunctions.
Figure 7H:
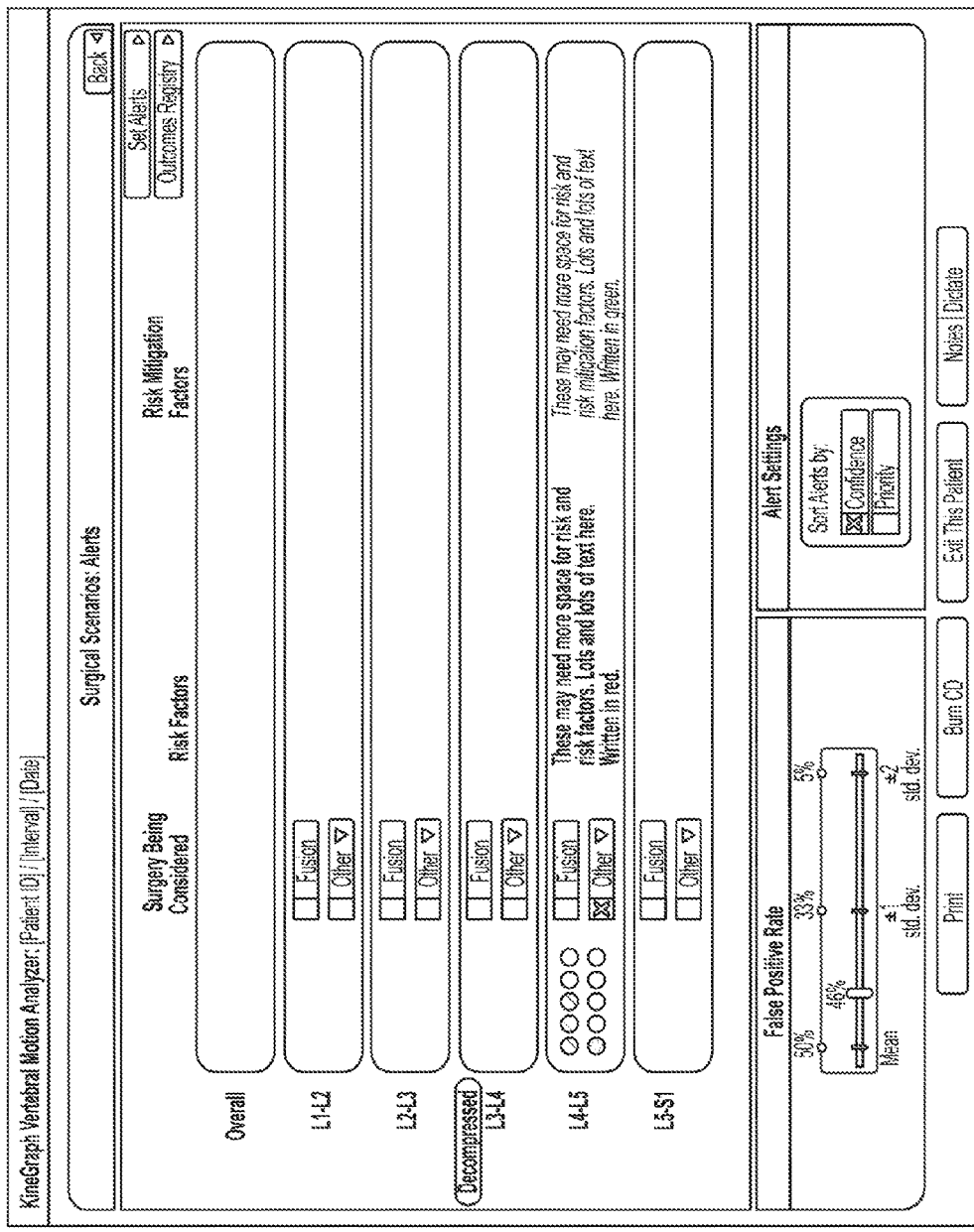
FIG. 7h is an example screen shot that illustrates the capability for viewing and interacting with surgeon alerts, as part of an alerts capability of the clinical data reporting software interface.

The results viewer also enables a user to interact with quantitative data regarding the detection of specific kinematic dysfunctions. FIG. 7g shows a screen shot 750 representing an example of this capability. In this figure, the results viewer affords the user several analytic capabilities, such as the ability to vary the statistical threshold limits with which abnormalities are detected. For example, if a "False positive rate" is set to 5%, only patients below $2.5^{th}$ percentile or above $97.5^{th}$ percentile (relative to a normative dataset collected from asymptomatic subjects) would be considered abnormal. If this "false positive rate" were to be changed to 10%, the threshold limits would then change to below the $5^{th}$ percentile or above the $95^{th}$ percentile, and so on. Another capability is to present graphic icons which represent specific kinematic abnormalities, then either presenting these icons or not depending on whether the abnormality is detected based on the specific threshold limit set by the user. Another capability is to view measurement data graphically and numerically. Different data from different bending modes can be accessed via this capability, and the user is provided with tools to let them determine which data to view.

As shown in FIG. 7G alerts can be presented to the user as a graphic presentation. An embodiment of this capability is represented in the screen shot 760. As described above, the statistical threshold limits with which abnormalities are detected can be varied by the user, and the resulting changes to the list of surgical alerts which are triggered are presented to the user in real time.

The clinical data reporting software system provides a process of creating a centralized aggregate database allowing for data input, viewing and querying that can be used by the user to compare potential clinical outcomes of the subjects.

Figure 8A:
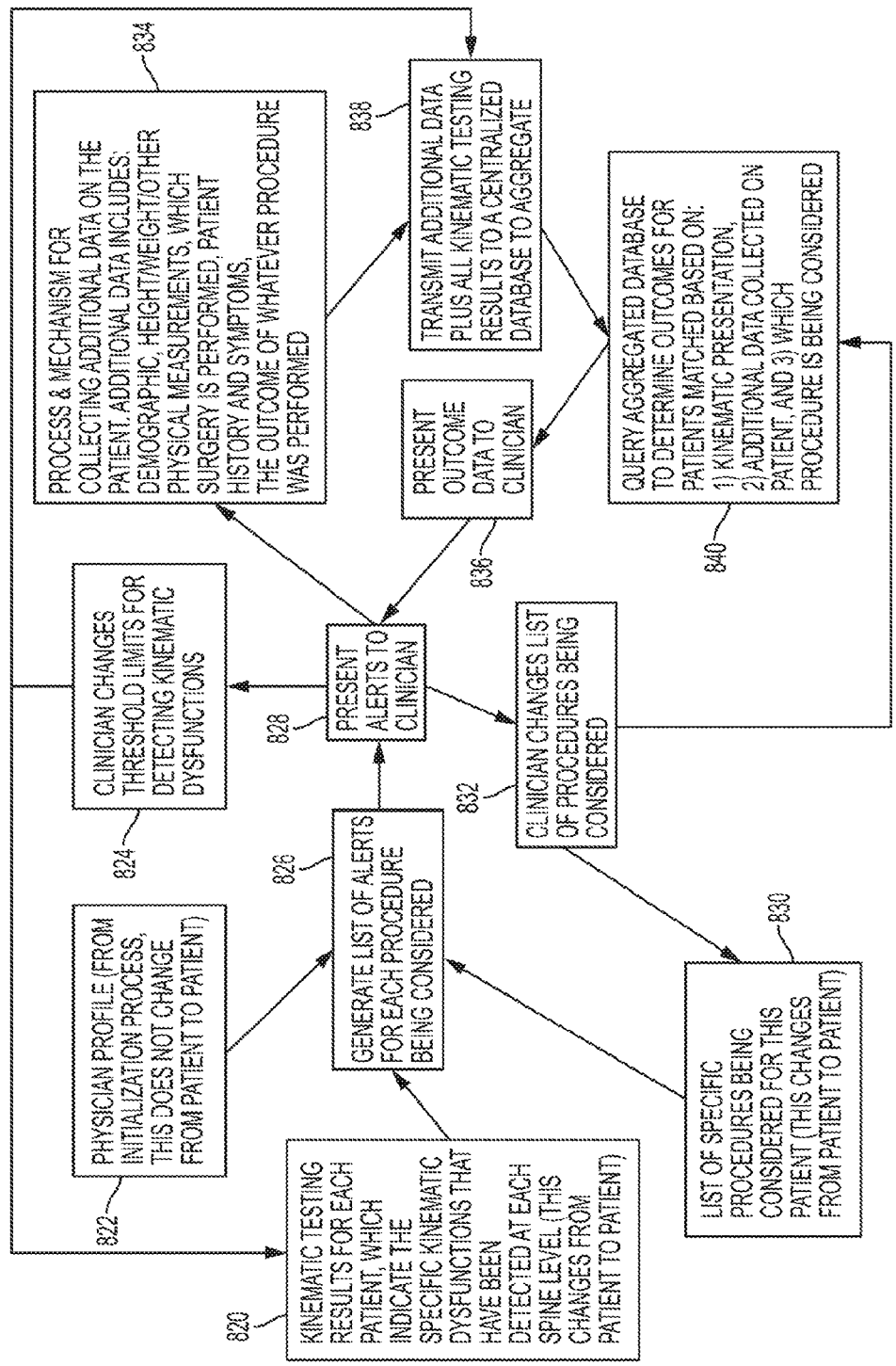
FIG. 8a is a block diagram outlining a process within the clinical data reporting software interface for creating a centralized aggregate database allowing for data input, viewing and querying that can be used for consideration and comparison of patient outcomes.

FIG. 8a is a simplified block diagram outlining the process and mechanism for inputting additional data on each subject to include, such data to include: demographic, height/weight/other physical measurements, subject history, symptoms, neurological exam results, other co-morbidities at each level, other systemic patient co-morbidities (such as diabetes, for example), prior procedures performed and their related outcome(s), as well as other parameters, and a process for transmitting this additional data to an aggregated database. The system provides a process for collecting data from all subjects tested, creating an aggregated database that can be used for consideration and comparison of outcomes for subjects matched based on: 1) kinematic presentation, 2) additional data collected, and 3) procedure being considered. The predicted outcome data is presented to the user and can be used to modify inputs to start the process over again with a new series of inputs if desired.

For patients who get tested, there is an additional process that allows the user (surgeon/clinician) to input additional data, then view data regarding potential clinical outcomes of procedures being considered by querying the aggregated database. Kinematic testing results for each patient, which indicates the specific kinematic dysfunction that has been detected, for example, at each spine level 820 communicates with a query aggregated database 840 to determine outcomes for patients matched based on kinematic presentation, additional data collected on the patient, and the procedure being considered. The user can change the list of procedures being considered 832 which changes the list of specific procedures being considered for a specific patient 830 which in turn impacts the list of alerts generated for each procedure being considered 826. The list of alerts 826 also factors in the user profile from the initialization process 822. When alerts are presented to the user 828 it is possible for the clinician to change threshold limits for detecting kinematic dysfunctions 824, which can impact the query aggregated database 840. Additional data may also be collected from the patient 834 which can then be transmitted to the centralized database 838 and presented to the user 836.

Figure 8B:
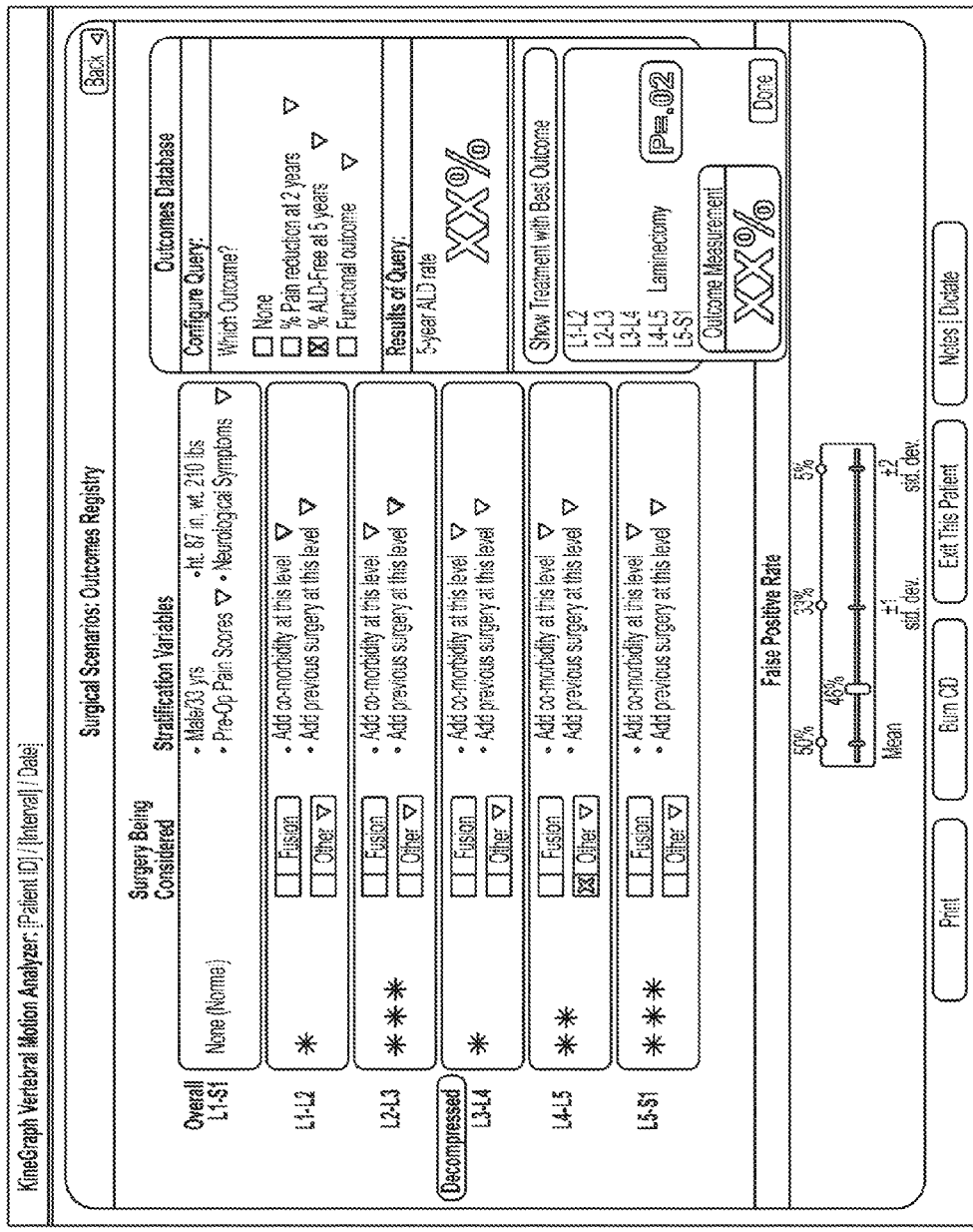
Figure 8C:
Figure 8D:
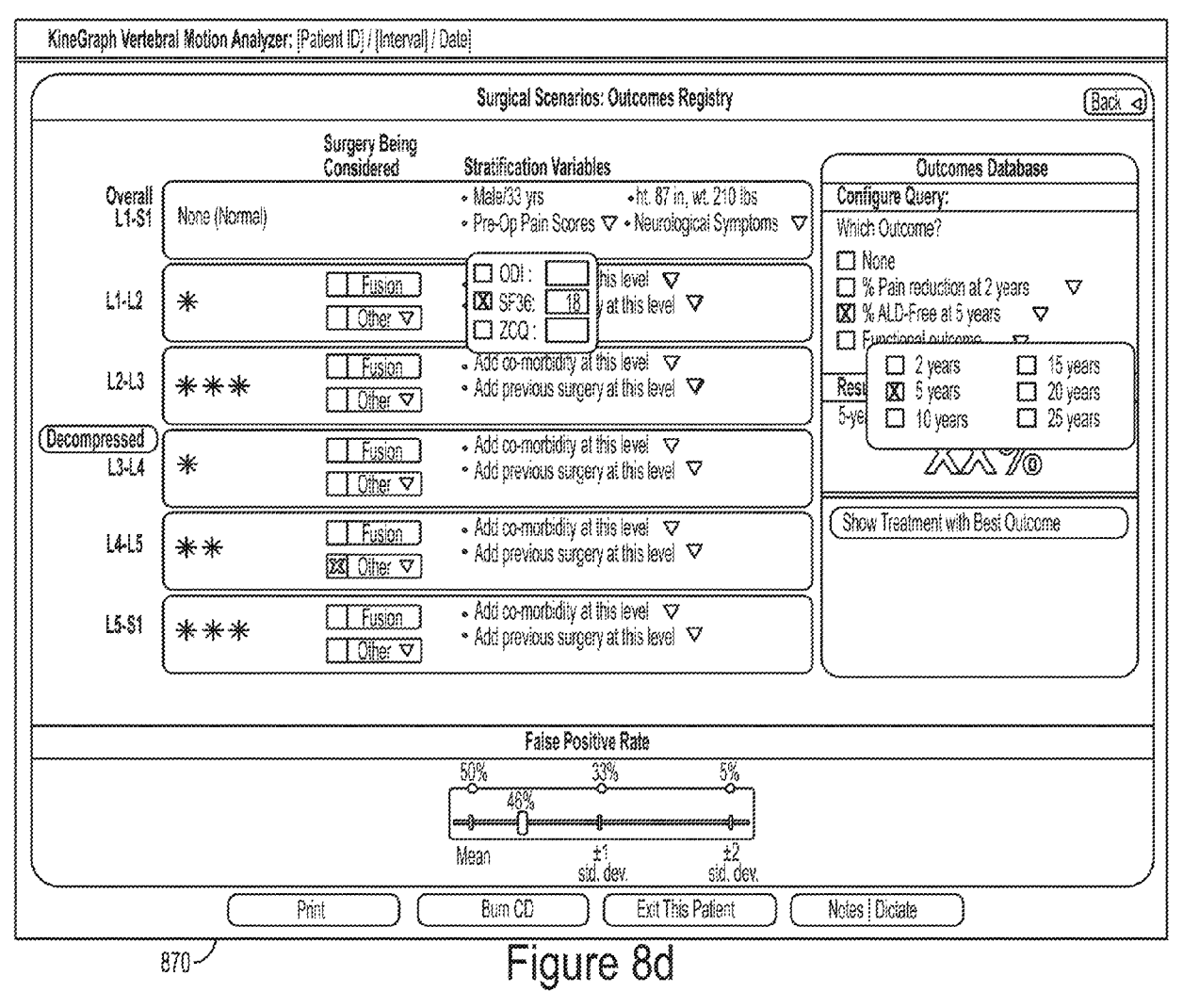

FIG. 8b is a screen shot 850 that illustrates a process of creating a centralized aggregate database via data input, viewing and querying that can be used by the user to compare potential clinical outcomes of the subject. During the process step, the user changes to a list of procedures being considered which is depicted as being accomplishable by checking boxes and drop down menus of procedures being considered at each spine level. The process step process and mechanism for inputting additional data on each subject is depicted as being accomplishable by checking various boxes and drop down menus listed on the form. The process step present outcomes data to user is depicted as being accomplishable via a series of drop down menus and check boxes which allow the user to specify which outcome measurement is being assessed (pain relief at 2 years, for example), and the output data are presented in terms of a percentage that had good pain relief. In FIG. 8c a screen shot 860 for inputting neurological exam results into the aggregated database is shown. FIG. 8d a screen shot 870 for inputting a patient's pain scores into the Aggregated Database, as well as a process and mechanism to select among various outcomes assessments to be output, are shown.

As an example, the clinical data reporting software system interprets kinematic results of subjects that were tested in a standing (active) or lying down (passive) position, which allows for isolating the muscle or load contribution, generating and/or interfacing with a computer model of biomechanics specific to a given subject. These computer models of biomechanics usually include anatomical and functional models, and by inputting patient specific data along with measurements of how kinematics were different between loaded active and unloaded passive bending, it can be possible to produce explanatory hypotheses that can explain the observed kinematics based on the anatomical and functional models.

Figure 9:
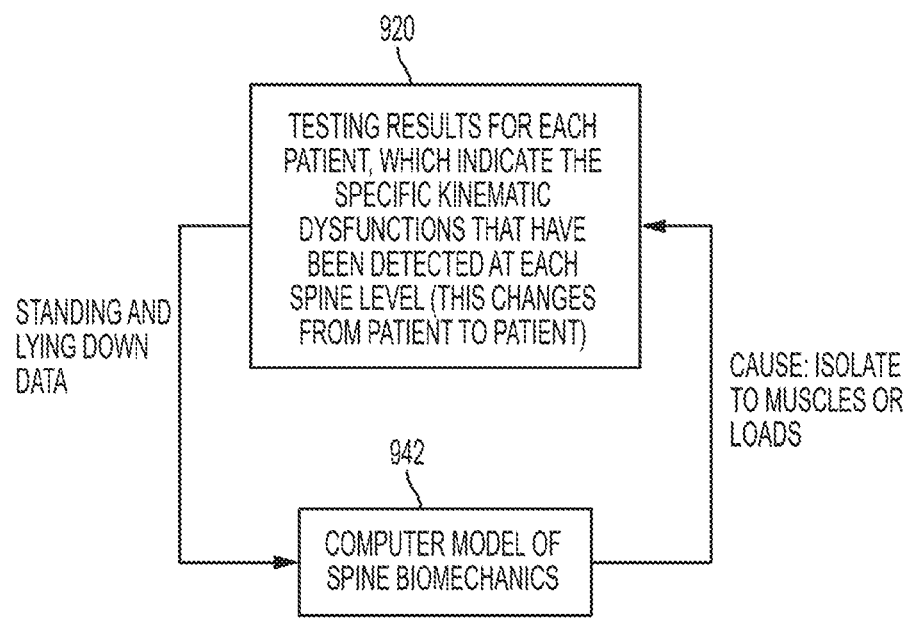
FIG. 9 is a block diagram outlining a process within the clinical data reporting software interface of interacting with a computer model of spine biomechanics based on patient-specific kinematic test data collected from subjects in a standing or lying down position, allowing for isolating muscle or load contribution which can help users further isolate the potential causes of joint pain or performance problems.

FIG. 9 is a block diagram outlining the process of isolating the cause of any observed dysfunction to either loads or muscles by use of a computer model of spine biomechanics 942, such as a finite element analysis or a model simulating soft tissue dynamics (such as the ANY-BODY MODELING SYSTEM™, manufactured by Anybody Technologies, Aalborg, Denmark), combined with kinematic test data collected from subjects in a standing and lying down position 920, which can influence the clinical treatment decision of the user by providing data customizable to each patient as to how the patients muscles are functioning.

One skilled in the art will appreciate that only one embodiment of the patient data recording software interface is represented in the above description, and there are many other alternative embodiments of different joints other than the spine, different mammalian animals other than humans, different embodiments and designs other than those presented to accomplish the essential function described herein.

B. Surgical Navigation and Patient Positioning

Systems and methods are also contemplated for registering, for example, spinal motion data to an instrument-supported therapeutic procedure, such when using surgical planning, assistance and/or surgical navigation systems. The systems and methods use the platform disclosed in FIGS. 1-5 above in combination with surgical planning, assistance and/or navigation systems as well as with patient positioning systems. Additionally, the systems and methods can be configured to communicate with surgical planning, assistance, and/or navigation devices and system as well as with patient positioning systems. Surgical navigation systems include, for example, robotic surgical instrument systems. Suitable systems include, for example, a plurality of articulating arms having at least two articulation joints, where the articulating arms are adapted to be inserted into an operative space in a substantially straight configuration and further adapted to controllably articulate inside the operative space, with at least three degrees of freedom of movement; at least one access port adapted to receive the articulating arms; and a controller adapted to control the articulation of the articulating arms inside the operative space to perform a surgical procedure. See, for example, U.S. Patent Pub. 2011/0238080 by Ranjit et al. published Sep. 29, 2011, entitled Robotic Surgical Instrument System; U.S. Pat. No. 7,996,110 by Lipow et al. issued Aug. 9, 2011, for Surgical Robot and Robotic Controller; U.S. Pat. No. 7,865,269 by Prisco et al. issued Jan. 4, 2011, for Robotic Surgical System and Joint Motion Controller Adapted to Reduce Instrument Tip Vibrations; and U.S. Pat. No. 6,228,089 to Wahrburg issued May 8, 2011, for Device for Positioning and Guiding a Surgical Instrument During Orthopedic Interventions.

The therapeutic procedure can comprise of instrumentation that facilitates a pre-determined therapeutic outcome. For example, spinal motion and intra-vertebral articulation can be determined by a kinematic measuring system. The motion data can then be transferred and registered to an automated or mechanical device. Suitable instruments include a surgical navigation system, which is automated or manually operated, or combinations thereof. Surgical navigation systems include, for example, StealthStation® iNAV™ or iOR™ or Treon™ or TRIA™, available from Medtronic or PiGalileo™ Computer-Assisted Orthopedic Surgery System available from Plus Orthopedics. Moreover, the therapeutic procedure may or may not include surgical implants, such as where a therapy is targeted at matching pre-determined outcome to therapy. Inter-vertebral motion data can also be acquired manually or via an automated system. The system can also be adapted and configured to acquire both static and dynamic parameters. As will be appreciated by those skilled in the art, data to be transferred can be manually or automatically transferred. An optimal position and orientation outcome of the spine can also be determined by the system and transferred within the system or to another system or user. In at least some embodiments, the such surgical navigation system operates such that it can maintain orientation and position in up to 6 degrees of freedom: moving up and down (heaving); moving left and right (swaying); moving forward and backward (surging); tilting forward and backward (pitching); turning left and right (yawing); and tilting side to side (rolling).

Figure 10:
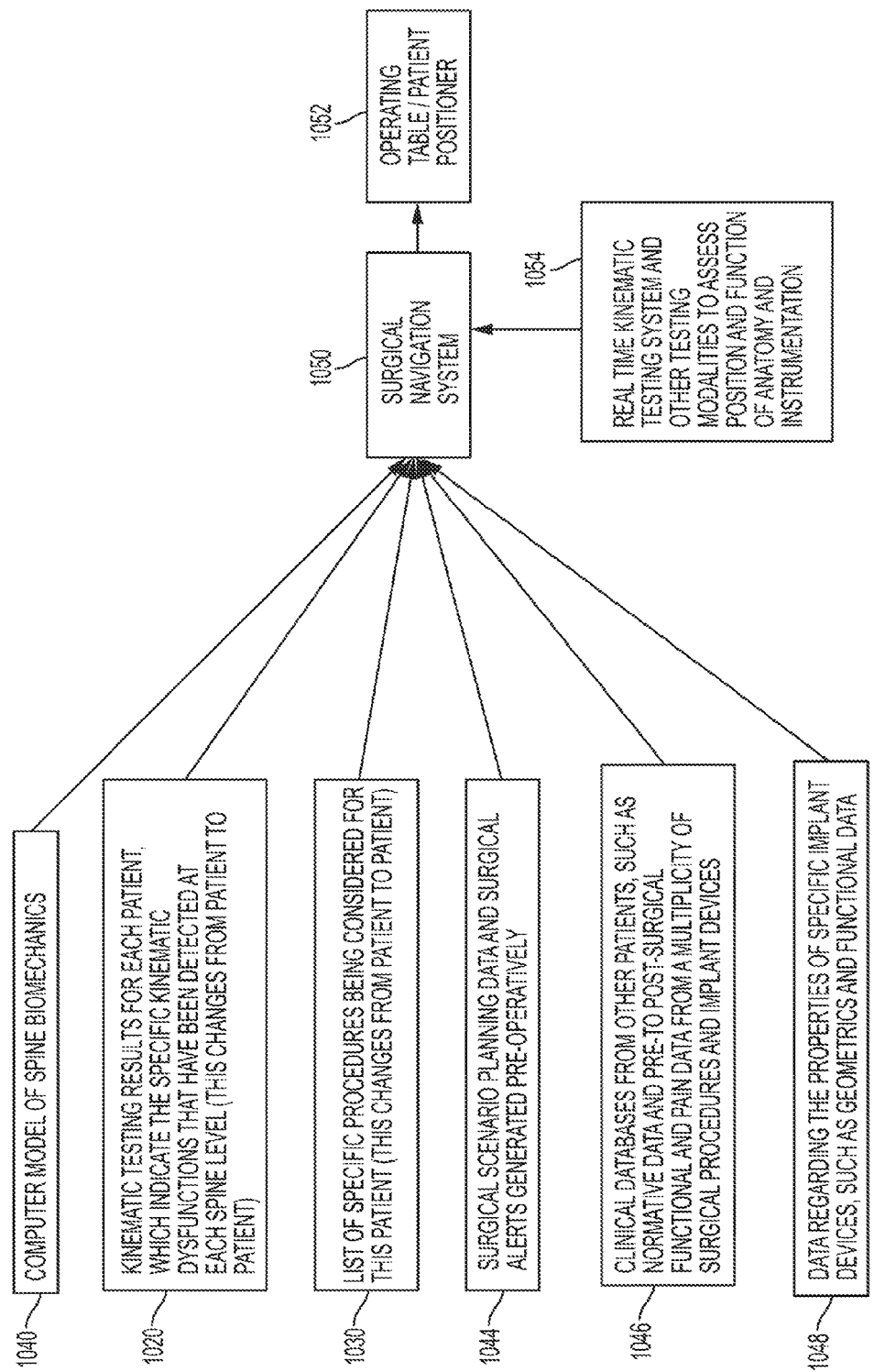
FIG. 10 is a block diagram showing system components and inter-connections of a surgical navigation and patient positioning system.

A variety of implants, such as spinal implants, can be used with the system, including devices that fuse the spine or facilitate motion preservation. Such implants can have pre-determined optimal specifications for position and orientation FIG. 10 is a simplified block diagram showing system components and inter-connections of an embodiment of the present disclosure that involves the integration of a clinical data reporting software component with a surgical navigation system. In such an integral system there would be three classes of input information. First, data can be recorded directly from the patient, which could include such diagnostic data as 1020, kinematic data collected from the subject as well as generating a computer model of spine biomechanics 1042, such as one that has been programmed with patient-specific parameters. Additionally, data could also recorded directly from the surgeon or treating physician, such as surgical scenario planning data 1044, surgical alerts generated pre-operatively, and a list of specific procedures being considered for the patient 1030. In additional aspects, data can be collected from sources external to the subject and the physician/surgeon, such as queries of previously-collected clinical databases 1046 such as normative data and pre- to post-surgical functional and pain data as well as data regarding the properties of specific implant devices 1048, such as geometric and functional data. All of these input datasets feed data into a surgical navigation system 1050, such as those that are currently commercially available such as NAVIGATION SYSTEM II (Stryker Instruments, Dallas, Tex.) and STEALTHSTATION S7 (Medtronic Navigation, Louisville, Colo.) or any of the other surgical navigation systems mentioned previously in this section. Surgical navigation systems can also include neuro-monitoring systems such as the NVJJB/M5 system (Nuvasive, San Diego, Calif.). Having this input data available for use for a surgical navigation system is extremely advantageous, because it enables several novel and inventive new capabilities. For example, surgical implant device placement and/or surgical approach could be informed by patient specific geometric or functional factors that are currently not available. Data collected from previous clinical studies could be applied during surgery through an iterative navigational process accomplished by the surgical navigation system 1050 to optimize device placement and surgical approach with a multitude of potential goals: (i) to achieve placement and/or function as close to normative values as possible; (ii) to achieve a specific type of functional outcome; (iii) achieve parameters appropriate to a specific type of device design; (iv) to maximize the chance of reducing pain; and (d) any combination of the above, plus others.

The surgical navigation system 1050 may also then connect with an operating table/patient positioner 1052. This operating table/patient positioner 1052 is then able to communicate data to and from the surgical navigation system (to: control data to control to position of the patient and other data; from: data regarding position of the patient, and other data), which in turn is in communication with one or more of the various components (e.g., computer model, kinematic testing results, specific procedures being considered, surgical scenario planning, clinical databases, data regarding specific contemplated implants, and/or kinematic testing system). This operating table/patient positioner 1052 can then be used to put the patient into a specific posture during a surgical operation based on parameters determined via the surgical navigation system 1050 or any of the components with which the surgical navigation system 1050 is in communication. A feedback loop is also contemplated, wherein real time kinematic testing system and other testing modalities to assess position and function of anatomy and instrumentation can be collected from the patient 1053 and is communicated to the surgical navigation system 1050, which can then utilize this data to adjust either parameters within the surgical navigation system 1050, or parameters within the operating table/patient positioner 1052. Such real time kinematic testing systems 1054 could include imaging modalities, position sensors, motion sensors, electromyography data collection devices, and a host of other data collection devices. In an alternative embodiment, the operating table/patient positioner 1052 can be connected directly to the various components of the system (e.g., computer model, kinematic testing results, specific procedures being considered, surgical scenario planning, clinical databases, data regarding specific contemplated implants, and/or kinematic testing system) without the use of a surgical navigation system (for such a configuration, all of the connections going into the surgical navigation system 1050 would instead connect directly to the patient positioner 1052, thus bypassing the surgical navigation system 1050).

Figure 11:
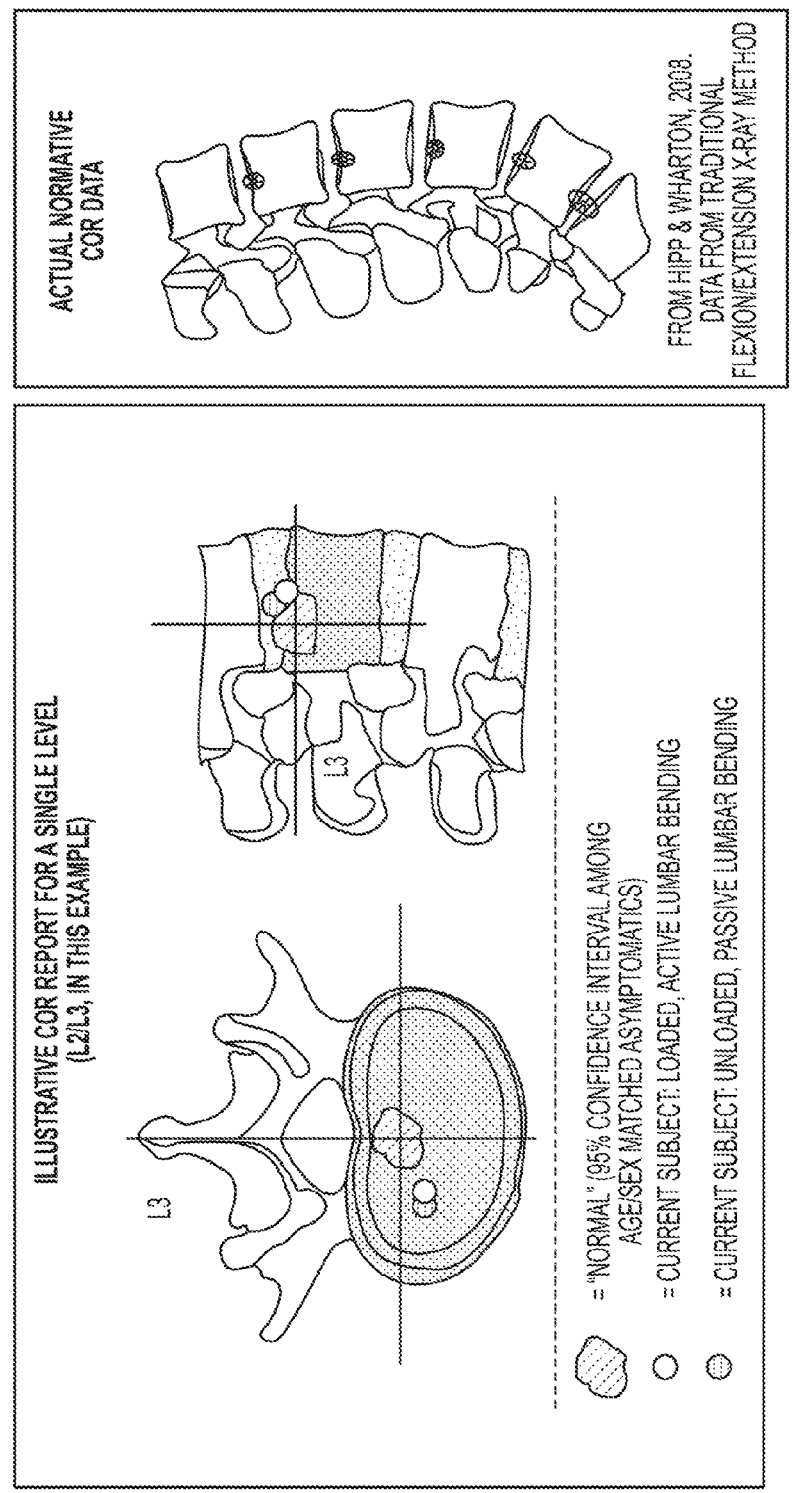
FIG. 11 is an illustration of a center of rotation report for a single level in the spinal column, which could come from the measurement system and be used as a parameter in optimizing the balance of the spine post-operatively via deterministic geometry and orientation of a surgical construct accomplishable via a surgical navigation system working in combination with the surgical navigation and patient positioning components.

FIG. 11 shows the center of rotation concept as it applies to lumbar spine levels. Center of Rotation (COR) is a point (x, y) on a plane (sagittal and transverse) that corresponds to the "fulcrum region" of a vertebral level (i.e. where forces are concentrated during motion). The present disclosure could use COR measurements for each patient in loaded active (i.e. muscle-involved) bending and unloaded passive (i.e. no muscles involved) bending. Coronal and sagittal plane COR measurements could be taken, transverse plane COR can also be derived from these. Normative measurements (i.e. what is "normal"), based on clinical trials conducted on asymptomatic subjects are represented graphically. One way this is valuable to users is to know how COR changes from standing to lying: surgeons operate on patients while they are lying down, however their targets are usually based on normal operating conditions (which are standing up). Therefore knowing how a given parameter, such as COR, changes from standing to lying can help the surgeon achieve a target standing COR based only on the geometry and orientation of the anatomy in the lying posture.

FIG. 12 is a table that describes, according to one embodiment of the present disclosure, some ways in which functional targets could be valuable in a surgical navigation system intended for spine surgery. For example, the navigation target could be the location and orientation of the superior and inferior endplates of a fusion construct. In this case the biomechanical goal would be to ensure that adjacent level CORs are as close to "normal" as possible. The clinical benefit would therefore be to avoid abnormal facet loading (if COR is too anterior), off-loading (if too posterior), and left/right imbalances. In another example, the navigation target would be the placement of inter-body and motion preserving devices on vertebral endplate. In this case the biomechanical goal would be to ensure device overlaps with COR of the joint, aligning forces through the device and avoiding problematic moment arms. The clinical benefit would include: (1) to take advantage of Wolf's law to optimize bone in-growth, and/or (2) to reduce stressing moment arms to avoid failure of construct.

Figure 13:
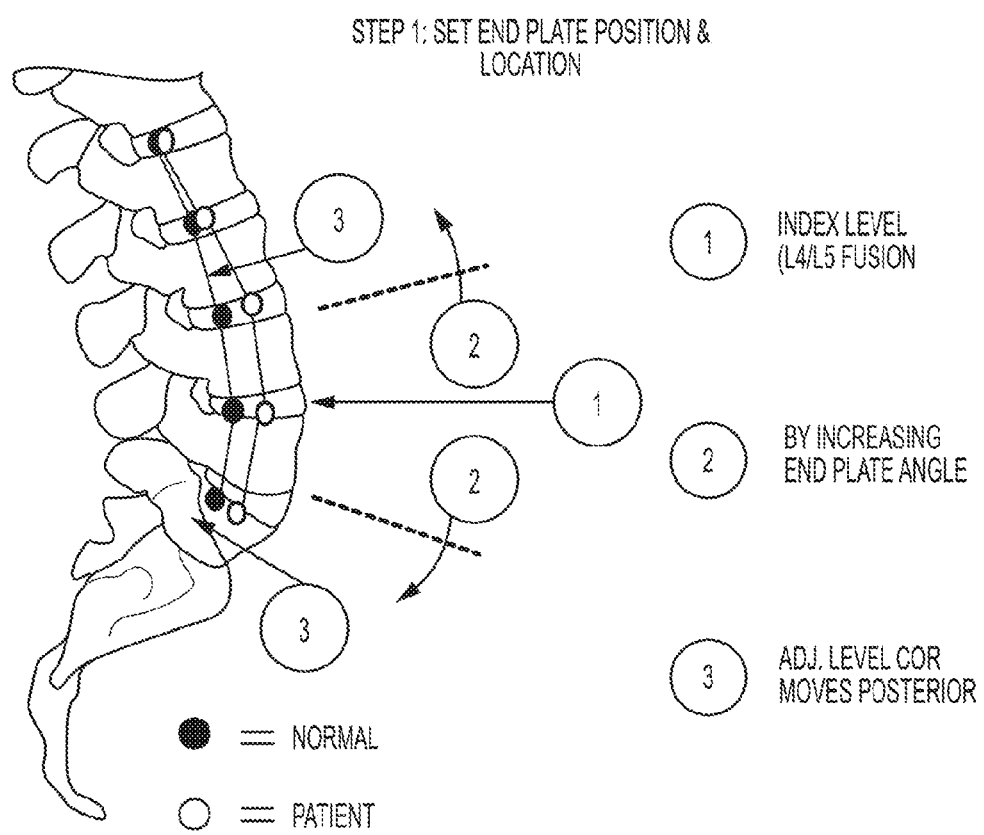
FIG. 13 illustrates a first step of a two step process for achieving position and geometry of a spine fusion surgical construct via the surgical navigation and patient positioning.

FIG. 13 shows step one of a hypothetical example two step process in which functional targeting could be utilized in a spine surgical navigation system. In this figure, a sagittal plane routine is described wherein the desired position and location of endplates is achieved via device sizing and placement distraction or compression along posterior rods. By varying the geometry of the fusion construct, the COR at adjacent levels can be affected such that they are moved into an orientation that is deemed to be more optimal by the surgeon, based on for example the location that is observed in asymptomatic subjects. A similar routine could be done for coronal pane. This demonstrates an example workflow for a fusion construct; similar workflows could be accomplished for other spine surgical constructs (motion preserving, interspinous devices, etc) as well as for other joints.

Figure 14:
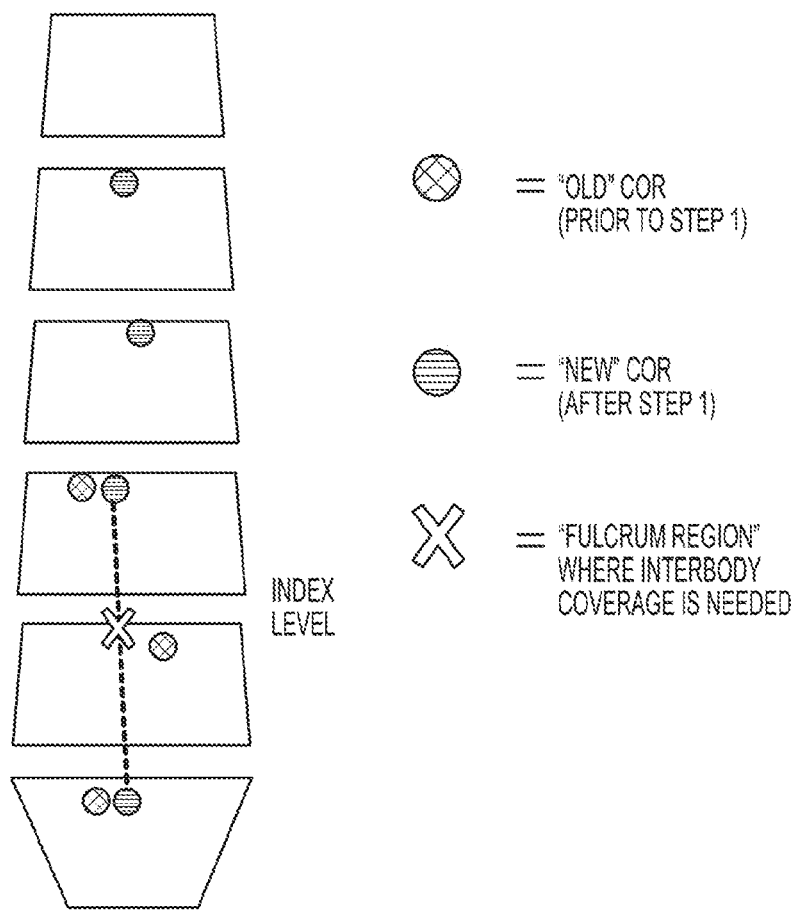
FIG. 14 illustrates a second step of a two step process for achieving position and geometry of a spine fusion surgical construct via the surgical navigation and patient positioning.

FIG. 14 shows step two of a hypothetical example two step process in which functional targeting could be utilized in a spine surgical navigation system. According to this figure, Step two of the two step process is to modify the fusion construct as necessary to ensure coverage by an interbody device of the fulcrum region of the fused level. This is accomplished via several sub-steps: (a) project new "connector lines" between the "new" locations of the COR of the adjacent levels; (b) Determine the region on superior endplate of the inferior vertebra of the index level (L5 in this case) endplate where "new" COR connector lines intersect (marked "x"); (c) this is the "fulcrum region" that needs to be "covered" by the interbody device; (d) Adjust interbody construct to ensure "coverage" of the "fulcrum region"; (e) This is shown for coronal plane; a similar routine is also done for the sagittal plane. Although FIGS. 13 and 14 contemplate this process applied to a fusion surgery, one skilled in the art would appreciate that there are multiple other embodiments which could be directed to: optimize the fusion construct geometry based on different parameters than COR, optimize the fusion construct based on other uses of COR, optimize other types of surgical constructs associated with other types of surgeries for COR and other parameters.

The inputs, information and reports can be transmitted through either a direct wire-based electronic connection between the two or more components, or through a wireless connection, and can be of the type that is derived from computer programming or from operator, user or subject input, or from a combination of computer programmed information plus operator, user and/or subject input.

C. Imaging System Moveable within a Vertical Plane

The imaging system moveable within a vertical plane is an apparatus providing input image data for the measurement system that assists with imaging during joint operation. It consists of a medical imaging system mounted to a free floating, ballasted vertical plane, so that the medical imaging system can be moved in tandem with the motion of the joint to keep joint anatomy within a field of view (for example keeping a knee in a field of view as a live human testing subject is walking) It can be operated in a manual or automatic mode, as further described below.

Figure 15:
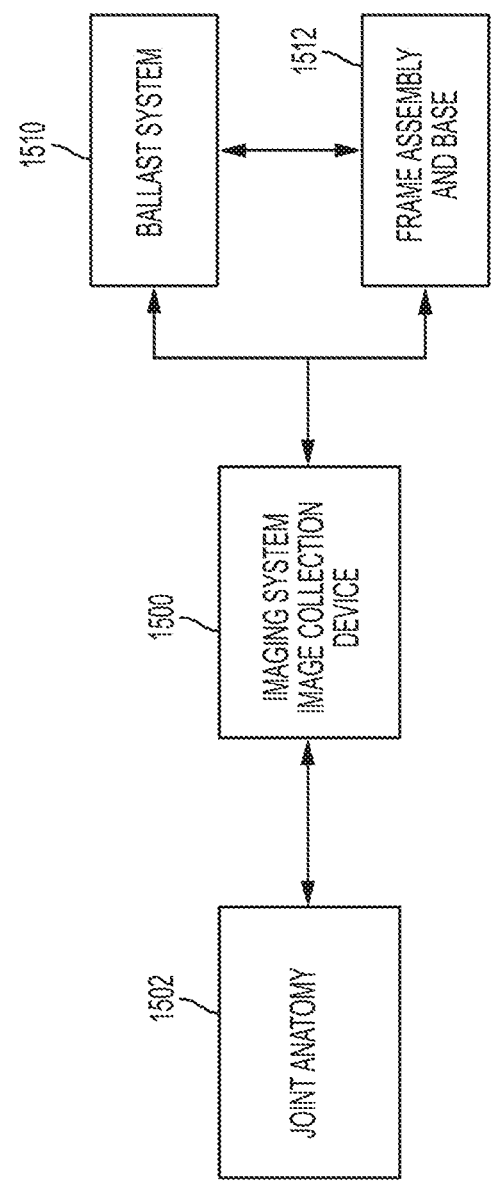
FIG. 15 is a block diagram of an imaging system moveable within a vertical plane, operating in manual mode.

FIG. 15 is a block diagram of an imaging system moveable within a vertical plane, operating in manual mode. The imaging system image collection device 1500 could be an image intensifier, a flat panel detector, or any number of other medical diagnostic image collection devices. The imaging system image collection device 1500 is free to move within a vertical plane, via movable connectors to a frame assembly 1512 and base that rests upon the floor. Ballast system 1510 and frame assembly base 1512 are connectable via a movable connector, such as linear bearings, that allow for the motion of the imaging system image collection device 1500 motion within a vertical plane. The ballast system 1510 can be rigidly connected to the frame assembly and base 1512, and movably connected to the imaging system image collection device 1500 such that the weight of the imaging system image collection device 1500 is fully ballasted. With the ballast system 1510 engaged, the only forces required to move the imaging system image collection device 1500 within the vertical plane are those required to overcome the devices inertia. The target joint anatomy 1502 for a particular procedure, a knee for example, is then connected to the imaging system image collection device 1500, such that the entire joint region of interest can remain in the field of view for the imaging of the joint during operation. The joint can be connected in such a manner as to reduce extraneous movement outside a desired target range of motion.

Figure 16:
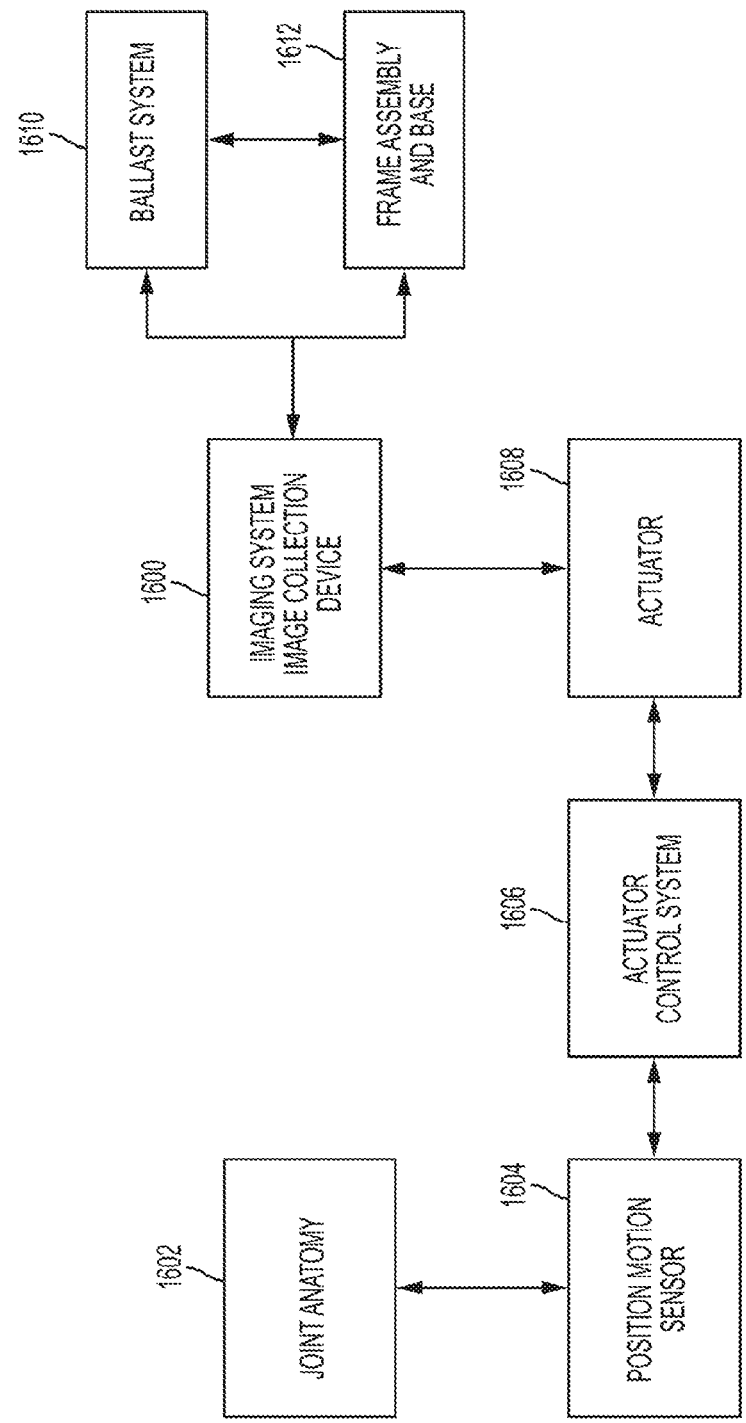
FIG. 16 is a block diagram of an imaging system moveable within a vertical plane, operating in automatic mode.

FIG. 16 is a block diagram of the imaging system moveable within a vertical plane, operating in automatic mode. In automatic mode, the descriptions of the components and the connections between them are no different than for manual mode, for components imaging system image collection device 1600, ballast system 1610, and frame assembly and base 1612. In manual mode, it is the motion of the joint, as transmitted via a connection such as a rod, that provides the forces to move the imaging system image collection device 1600. However, in automatic mode this is accomplished via an actuator 1608 that is connected to an automatic control system 1606. The automatic control system or actuator control system 1606 receives signals coming from the position/motion sensor 1604, which in turn is connected to a target joint anatomy 1602, such that the position/motion sensor 1604 senses the motion of the target joint anatomy. The automatic control system 1606 is then able to process this input data and produce control signals cause an actuation of the actuator 1608 to move the imaging system image collection device 1600. Overall, the motion of the imaging system image collection device 1600 should track the motion of the target joint anatomy such that the entire joint region of interest can remain in the field of view even as the joint anatomy 1602 moves relative to the frame assembly and base 1612. The actuator 1608 connects to the imaging system image collection device 1600 such that it can affect its motion within a vertical plane. The actuator 1608 is connected or connectable to the actuator control system 1606 and the position/motion sensor 1604, via a connection sufficient for transmitting control signals and position/motion data, such as a wired or wireless connection. The actuator control system 1606 is an electronic control system, such as a programmable logic controller or a laptop computer, that is capable of processing position and motion signals coming from both the position/motion sensor 1604 as well as from the actuator 1608, and of producing actuator control signals to affect a motion as described herein.

The image data can be transmitted through either a direct wire-based electronic connection between the two or more components, or through a wireless connection, and can be of the type that is derived from computer programming or from operator, user or subject input, or from a combination of computer programmed information plus operator, user and/or subject input. One skilled in the art will appreciate that there are many shapes, sizes, and configurations of the imaging system moveable within a vertical plane required for various mammalian joints.

A collimator device 1713 may be optionally attached to either or both of the attachment arms 1701 and/or 1705 for use in the case of ionizing radiation based imaging modalities. This collimator device is intended to block the path of ionizing radiation for one or both of two purposes: (1) minimize the dose of absorbed radiation on the part of the patient, and (2) minimize "flare", which can degrade the contrast of medical images and can occur when X-rays pass unimpeded from the source to the detector without first passing through the patient. This collimator device is composed of a leaded material or some other material with sufficient density as to partially or completely block ionizing radiation from passing through it. Stationary collimator devices that do not adjust during imaging are not useful, as the field of interest within the imaging frame changes as the joint of interest is in operation during testing. Therefore the collimator device 1713 is intended to maintain a changing field of interest within the imaging frame as the position of the patient's anatomy changes as a function of normal joint operation, such that "flare" and radiation dose to the patient are both minimized while not obscuring any of the physiologic structures of interest. In one embodiment, the collimator connects to both attachment arms 1701 and 1705 according to FIGS. 17A-B so that only specific band around each attachment arm is imaged. For situations in which it is feasible, it is ideal to place the collimator between the patient and the radiation source so as to block radiation that would have imaged parts of the patient's anatomy that are not of interest for the prescribed diagnostic study. The collimator device 1713 may also incorporate an actuator that is intended to change the position and geometry of the shielding pieces dynamically during the tested motion. This actuator can be controlled by an electronic control system that incorporates stored input data or real time input data, both data coming from other parts of the motion control device or from another device such as an imaging device or a posture assistance device. The purpose of this functionality of the collimator device is to capable of dynamically adjusting the geometry of the shield during tested motion so as to maximize the benefit of the collimator device in terms of reducing radiation dose to the patient or in terms of reducing "flare", or both.

The apparatus can further be adapted and configured to keep a specific part of the patient's anatomy within the imaging field of interest during imaging. This can be accomplished by an imaging field adjustment mechanism capable of calculating the positional adjustments necessary to keep the joint of interest within and/or centered within the imaging field, then producing a movement between the support frame base 1717 and the support frame vertical member 1715, such that the specific part of the patient's anatomy is held within and/or centered within the field of imaging. In one embodiment, this imaging field adjustment mechanism would function as follows: (1) while attached to the apparatus, the patient is moved to extreme position #1 of the motion sweep that is being studied; (2) the apparatus is positioned relative to the medical diagnostic device such that the anatomy of interest on the patient is centered in the field of image of the diagnostic device; (3) this relative position between the imaging device and the apparatus is recorded as extreme position #1; (4) the patient is then moved to extreme position #2 of the motion sweep that is being studied; (5) this relative position between the imaging device and the apparatus is recorded as extreme position #2. Once these two extreme relative positions between the apparatus and medical diagnostic device have been recorded, the imaging field adjustment mechanism then affects a relative motion between the support frame base 1717 and the support frame vertical member 1715 from extreme position #1 to extreme position #2, and possibly back again, in such a way that this relative motion is synchronized with the motion sweep of the apparatus to hold a specific part of the patient's anatomy within and/or centered within the imaging field of interest. Furthermore, the calculation of motion between the support frame base 1717 and the support frame vertical member 1715 required to keep the anatomy of interest within the imaging field can be recorded and integrated into the computation of the range of motion of the specific joint of interest. In an alternative embodiment of the imaging field adjustment mechanism, an image centering marker is placed on the patient that denotes where the center of the imaging field should be positioned. The image centering marker interacts with the medical diagnostic device in such a way that the center of the imaging field always remains fixed on the image centering marker. So as to not interfere with the anatomy of interest, the image centering marker does not have to be in the actual center of the imaging field, but instead in a position within the image that remains relatively fixed throughout the motion. Data encoding devices can be optionally attached to either of the attachment arms 1701 and 1705 and/or the patient and data to be transmitted directly to the medical images or other diagnostic formats. During operation of the device, there are several sets of data that can be generated by the operation of the motion control device or by the operation of other devices used during testing, such as the attachment mechanisms 1703 and 1707, or the medical diagnostic device. Such data could include: time synchronization data which is data indicating the exact point in time when the motion device begins and ends a tested motion sequence or a surgical step; the position of each or both of the attachment arms 1701 and 1705, which could be a goniometer measurement, a protractor measurement, or a measurement of the displacement of each attachment arms 1701 and 1705 relative to the starting position or relative to the attachment mechanisms 1703 and 1707; parameters associated with the actuators, such as the level of applied force, displacement, velocity, or other parameters; the weight applied to the attachment arms 1701 and 1705 by the patient at any given moment; the force applied by the subject on the attachment arms 1701 and 1705 at any given moment; the displacement, velocity, or other parameters associated with the imaging field adjustment mechanism, or any other measurement parameter that is relevant to the tested motion and that can be generated by, for example, sensors included within the motion control device or by an input from a data source external to the motion control device, such as the medical diagnostic device. The data encoding device may either be mechanical or digital devices that are capable of producing discernable analog or digital markings within the field of imaging that therefore get captured on the medical images resulting from the operation of the present disclosure (when the medical diagnostic device is a medical imaging device) that: (1) do not interfere with part of the field of imaging of interest for the prescribed diagnostic study, (2) can transmit data via the image that can be decoded at a later point in time such that all encoded data can be derived entirely through an analysis of each medical image. In one embodiment of the present disclosure using X-ray based fluoroscopy imaging, the data encoding device can be a radio-opaque protractor showing the angular displacement of the attachment arms 1701 and 1705, or alternatively could be a radio-opaque analogue needle-gauge to measure the current through the actuator at any point in time.

Different orientations of the diagnostic imaging system: The present disclosure contemplates a mechanism adapted and configured to perform diagnostic imaging of a joint where the field of imaging is fixed in space; however a diagnostic imaging system that does not have a field of imaging that is fixed in space could also be utilized. In such a case, the diagnostic imaging equipment would be operably moveable so that the field of imaging does not stay fixed in space, but instead would stay fixed with respect to: (1) the motion platform, (2) a landmark on the subject, or (3) any trajectory defined by the operator.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. A system for producing optimized anatomical position data wherein the optimized anatomical position data is for use during spine surgery or during pre-operative planning, comprising a processor wherein the processor is configured to:
   receive one or more images of spinal anatomy generated by a medical imaging device;
   process measurements from the one or more images of the spinal anatomy to determine spatial relationships between vertebral bodies visible within an area of interest from the one or more images;
   determine for each of one or more spine joints targeted for a spinal fusion implantation procedure a projected optimal fixed segmental spatial relationship between vertebral body endplates of the one or more targeted spinal joints by
   (a) generating a projected post-surgical configuration for the spine anatomy by combining two data sets comprising:

(1) the measurements of the spatial relationship between vertebral bodies, taken from among the spine joints that are not targeted for the implantation procedure, and excluding data from the targeted spine joints; and (2) the projected optimal fixed segmental spatial relationship between vertebral body endplates for each targeted spine joint, (b) creating a comparison between the generated projected post-surgical configuration and a reference configuration, and (c) determining the projected optimal fixed segmental spatial relationships based on this comparison; and generate optimized segmental anatomical position data for use during spine surgery or during pre-operative planning for the vertebral body endplates for the one or more targeted spine joints.

2. The system of claim 1 wherein the one or more images are received from a computer system in communication with the medical imaging device.

3. The system of claim 1 wherein the one or more spine joints are two or more vertebral bodies.

4. The system of claim 1 wherein the area of interest is two or more vertebral bodies.

5. The system of claim 1 wherein system is in communication with a surgical navigation system.

6. The system of claim 3 wherein the implant position optimization system generates an output data for use by the surgical navigation system.

7. The system of claim 3 wherein the surgical navigation system sets a spatial relationship between the implantable device and the one or more spine joints targeted for the implantation procedure.

8. The system of claim 1 wherein a user revises the generated anatomical position data for an implantable device.

9. The system of claim 1 a wherein the comparison between the generated projected post-surgical configuration and the reference configuration includes a consideration of spatial parameters collected from images of patients in standing postures.

10. A surgical optimization apparatus for producing optimized anatomical position data comprising:

a user computing device having a machine readable medium stored on a non-transitory computer-readable medium configured to:

provide feedback for a surgical procedure comprising:

receiving two or more images of a spinal anatomy generated by a medical imaging device;

processing measurements from the one or more images of the spinal anatomy to determine spatial relationships between vertebral bodies visible within an area of interest from the one or more images;

determining for each of one or more spine joints targeted for a spinal fusion implantation procedure a projected optimal fixed segmental spatial relationship between vertebral body endplates of the one or more targeted spinal joints by (a) generating a protected post-surgical configuration for the spine anatomy by combining two data sets comprising: (1) the measurements of the spatial relationship between vertebral bodies, taken from among the spine joints that are not targeted for the implantation procedure, and excluding data from the targeted spine joints; and (2) the projected optimal fixed segmental spatial relationship between vertebral body endplates for each targeted spine joint, (b) creating a comparison between the generated projected post-surgical configuration and a reference configuration, and (c) determining the projected optimal fixed segmental spatial relationships based on this comparison; and generating optimized segmental anatomical position data for use during spine surgery or during pre-operative planning for the vertebral body endplates for the one or more targeted spine joints.

11. The surgical optimization apparatus of claim 10 wherein the two or more spine joints are two or more vertebral bodies.

12. The surgical optimization apparatus of claim 10 wherein the area of interest is two or more vertebral bodies.

13. The surgical optimization apparatus of claim 10 wherein the surgical optimization apparatus is in communication with a surgical navigation system.

14. The surgical optimization apparatus of claim 11 wherein the surgical optimization apparatus generates an output data for use by the surgical navigation system.

15. The surgical optimization apparatus of claim 11 wherein the surgical navigation system sets a spatial relationship between the implantable device and the two or more joints.

16. The surgical optimization apparatus of claim 10 wherein a user revises the generated anatomical position data for the implantable device.

17. The surgical optimization apparatus of claim 10 a wherein the comparison between the generated projected post-surgical configuration and the reference configuration includes a consideration of spatial parameters collected from images of patients in standing postures.

18. A machine readable medium containing instructions stored on a non-transitory computer-readable medium that, when executed by a computing device, cause the computing device to perform a method, the method comprising:

receiving one or more images of a spine anatomy generated by an imaging device;

processing measurements from the one or more images of the spinal anatomy to determine spatial relationships between vertebral bodies visible within an area of interest from the one or more images;

determining for each of one or more spine joints targeted for a spinal fusion implantation procedure a projected optimal fixed segmental spatial relationship between vertebral body endplates of the one or more spinal joints by (a) generating a projected post-surgical configuration for the spine anatomy by combining two data sets comprising: (1) the measurements of the spatial relationship between vertebral bodies, taken from among the spine joints that are not targeted for the implantation procedure, and excluding data from the targeted spine joints; and (2) the projected optimal fixed segmental spatial relationship between vertebral body endplates for each targeted spine joint, (b) creating a comparison between the generated projected post-surgical configuration and a reference configuration, and (c) determining the projected optimal fixed segmental spatial relationships based on this comparison; and generating optimized segmental anatomical position data for use during spine surgery or during pre-operative planning for the vertebral body endplates for the one or more targeted spine joints.

19. The machine readable medium of claim 18 wherein the two or more spinal joints are two or more vertebral bodies.

20. The machine readable medium of claim 18 wherein the area of interest is two or more vertebral bodies.

21. The machine readable medium of claim 18 wherein the machine readable medium is in communication with a surgical navigation system.

22. The machine readable medium of claim 21 wherein the machine readable medium generates an output data for use by the surgical navigation system.

23. The machine readable medium of claim 21 wherein the surgical navigation system sets a spatial relationship between the implantable device and the two or more joints.

24. The machine readable medium of claim 18 wherein a user revises the generated anatomical position data for the implantable device.

25. The machine readable medium of claim 18 a wherein the comparison between the generated projected post-surgical configuration and the reference configuration includes a consideration of spatial parameters collected from images of patients in standing postures.

26. A surgical optimization apparatus means for producing optimized anatomical position data for use during spine surgery or during pre-operative planning, comprising:
  a user computing device means configured to:
    receive one or more images of spinal anatomy generated by a medical imaging device;
    process measurements from the one or more images of the spinal anatomy to determine spatial relationships between vertebral bodies visible within an area of interest from the one or more images;
    determine for each of one or more spine joints targeted for a spinal fusion implantation procedure a projected optimal fixed segmental spatial relationship between vertebral body endplates of the one or more targeted spinal joints by
      (a) generating a projected post-surgical configuration for the spine anatomy by combining two data sets comprising: (1) the measurements of the spatial relationship between vertebral bodies, taken from among the spine joints that are not targeted for the implantation procedure, and excluding data from the targeted spine joints; and (2) the projected optimal fixed segmental spatial relationship between vertebral body endplates for each targeted spine joint,
      (b) creating a comparison between the generated projected post-surgical configuration and a reference configuration, and
      (c) determining the projected optimal fixed segmental spatial relationships based on this comparison; and
    generate optimized segmental anatomical position data for use during spine surgery or during pre-operative planning for the vertebral body endplates for the one or more targeted spine joints.

27. The surgical optimization apparatus means of claim 26 wherein the two or more joints are two or more vertebral bodies.

28. The surgical optimization apparatus means of claim 26 wherein the area of interest is two or more vertebral bodies.

29. The surgical optimization apparatus means of claim 26 wherein the surgical optimization apparatus means is in communication with a surgical navigation system.

30. The surgical optimization apparatus means of claim 29 wherein the surgical optimization apparatus means generates an output data for use by the surgical navigation system.

31. The surgical optimization apparatus means of claim 26 wherein the surgical navigation system sets a spatial relationship between the implantable device and the two or more joints.

32. The surgical optimization apparatus means of claim 26 wherein a user revises the generated anatomical position data for the implantable device.

33. The surgical optimization apparatus mean of claim 26 a wherein the comparison between the generated projected post-surgical configuration and the reference configuration includes a consideration of spatial parameters collected from images of patients in standing postures.

34. A system for producing optimized anatomical position data wherein the optimized anatomical position data is for use during spine surgery or during pre-operative planning, comprising a processor wherein the processor is configured to:
  receive one or more images of spinal anatomy generated by a medical imaging device;
  process measurements from the one or more images of the spinal anatomy to determine spatial relationships between vertebral bodies visible within an area of interest from the one or more images;
  determine for each of the one or more spine joints targeted for an implantation procedure an optimal fixed segmental spatial relationship between vertebral body endplates of the one or more targeted spinal joints by
    (a) generating a projected post-surgical configuration for the spine anatomy by combining two data sets comprising: (1) the measurements of the spatial relationship between vertebral bodies, taken from among the spine joints that are not targeted for the implantation procedure, and excluding data from the targeted spine joints; and (2) the projected optimal fixed segmental spatial relationship between vertebral body endplates for each targeted spine joint,
    (b) creating a comparison between the generated projected post-surgical configuration and a reference configuration, and
    (c) determining the projected optimal fixed segmental spatial relationships based on this comparison; and
  generate data to trigger user alerts for use during spine surgery or during pre-operative planning based on the optimal fixed spatial relationship.

35. The system of claim 34 wherein the user alerts are in the form of red and yellow indicator colors that are overlaid onto a software user interface.

36. The system of claim 34 wherein the user alerts are based on a comparison of the optimal fixed spatial relationships with a pre-determined or user settable values.

37. The system of claim 34 a wherein the comparison between the generated projected post-surgical configuration and the reference configuration includes a consideration of spatial parameters collected from images of patients in standing postures.

* * * * *